United States Patent
Probst et al.

(10) Patent No.: US 12,186,076 B2
(45) Date of Patent: Jan. 7, 2025

(54) OPTICAL BASED GLUCOSE SENSOR

(71) Applicant: Medtronic, Inc., Minneapolis, MN (US)

(72) Inventors: David L. Probst, Chandler, AZ (US); Mark R. Boone, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 227 days.

(21) Appl. No.: 17/171,474

(22) Filed: Feb. 9, 2021

(65) Prior Publication Data

US 2022/0248986 A1  Aug. 11, 2022

(51) Int. Cl.
*A61B 5/1455* (2006.01)
*A61B 5/145* (2006.01)
*A61B 5/1459* (2006.01)
*A61B 5/1486* (2006.01)
*A61K 49/00* (2006.01)
*A61B 5/00* (2006.01)

(52) U.S. Cl.
CPC ........ *A61B 5/14532* (2013.01); *A61B 5/1455* (2013.01); *A61B 5/1459* (2013.01); *A61B 5/14865* (2013.01); *A61K 49/0036* (2013.01); *A61B 5/686* (2013.01)

(58) Field of Classification Search
CPC . A61B 5/14532; A61B 5/1455; A61B 5/1459; A61B 5/14865; A61B 5/686; A61K 49/0036
See application file for complete search history.

(56) References Cited

U.S. PATENT DOCUMENTS 4,606,351 A * 8/1986 Lubbers ............. A61B 5/14532
  435/14
4,981,779 A * 1/1991 Wagner .................... C12M 1/34
  435/228

(Continued)

OTHER PUBLICATIONS

Alen Pasic, Miniaturized fiber-optic hybrid sensor for continuous glucose monitoring in subcutaneous tissue, Sensors and Actuators B: Chemical, vol. 122, Issue 1, https://doi.org/10.1016/j.snb.2006.05.010. (Year: 2006) (Year: 2006).*

(Continued)

*Primary Examiner* — Alex M Valvis
*Assistant Examiner* — Grace L Rozanski
(74) *Attorney, Agent, or Firm* — Shumaker & Sieffert, P.A.

(57) ABSTRACT

An example medical device includes an optical sensor, processing circuitry, an antenna, and a power source. The optical sensor includes a light source; a reference optical beacon having a first fluorophore that emits a first fluorescence proportional to a first concentration of a substance proximate the beacon; a test optical beacon having a reagent substrate that reacts with an analyte to produce the substance and a second fluorophore that emits a second fluorescence proportional to a second concentration of the substance proximate the test beacon; and a photodetector to detect the first and second fluorescence. The processing circuitry determines a difference between the first and second fluorescence, which is indicative of the concentration of the analyte. The antenna and power source enable the medical device to operate completely within a biological system for continuous analyte monitoring.

26 Claims, 9 Drawing Sheets

(56) References Cited

U.S. PATENT DOCUMENTS

| | | | |
|---|---|---|---|
| 5,605,152 | A | 2/1997 | Slate et al. |
| 5,710,630 | A | 1/1998 | Essenpreis et al. |
| 6,032,059 | A | 2/2000 | Henning et al. |
| 7,263,394 | B2 | 8/2007 | Wang |
| 8,088,595 | B2 | 1/2012 | Ibey et al. |
| 9,037,205 | B2* | 5/2015 | Gil .................. A61B 5/1459 600/316 |
| 9,354,226 | B2 | 5/2016 | Chinnayelka et al. |
| 9,693,720 | B2* | 7/2017 | Markle .............. A61B 5/14539 |
| 9,797,909 | B2 | 10/2017 | Paterson et al. |
| 9,839,378 | B2 | 12/2017 | Markle et al. |
| 9,993,187 | B2* | 6/2018 | Hajnsek ............ G01N 21/6486 |
| 2007/0292897 | A1* | 12/2007 | Yazawa ............ G01N 33/54386 435/7.9 |
| 2009/0103084 | A1* | 4/2009 | Sadik ................. G01N 21/643 356/318 |
| 2010/0145317 | A1 | 6/2010 | Laster et al. |
| 2011/0105866 | A1* | 5/2011 | Markle .............. A61B 5/14532 600/316 |
| 2013/0211213 | A1* | 8/2013 | DeHennis ......... A61B 5/14556 600/316 |
| 2015/0098866 | A1 | 4/2015 | Reynolds et al. |
| 2019/0284601 | A1* | 9/2019 | Chiu .................... C09K 11/07 |
| 2020/0103346 | A1* | 4/2020 | Zhang ................. C12Q 1/6874 |
| 2020/0129982 | A1* | 4/2020 | Zhou ..................... B03C 1/01 |
| 2021/0181118 | A1* | 6/2021 | Yi .......................... G01N 21/80 |

OTHER PUBLICATIONS

Jose F Sierra, Fluorimetric-enzymatic determination of glucose based on labelled glucose oxidase, Analytica Chimica Acta, vol. 368, Issues 1-2, 1998, pp. 97-104, https://doi.org/10.1016/S0003-2670(98)00197-4 (Year: 1997).*

Singh et al., "Enhancing the longevity of microparticle-based glucose sensors towards one month continuous operation," Biosens Bioelectron, Jan. 15, 2010, 16 Pages.

"FDA approves first continuous glucose monitoring system with a fully implantable glucose sensor and compatible mobile app for adults with diabetes," https://www.fda.gove/news-events/press-announcements/fda-approves-first-continuous-glucose-monitoring-system-fully-implantable-glucose-sensor-and-compatible-mobile-app-for-adults-with-diabetes, dated Jun. 21, 2018, Retrieved Jun. 16, 2020, 3 Pages.

Borisov, "Chapter 1: Fundamentals of Quenched Phosphorescence O2 Sensing and Rational Design of Sensor Materials," Quenched-phosphorescence Detection of Molecular Oxygen: Applications in Life Sciences, 2018, pp. 1-18.

International Search Report and Written Opinion of International Application No. PCT/US2022/015051, dated May 20, 2022, 14 pp.

Steiner et al., "Optical methods for sensing glucose," Royal Society of Chemistry, vol. 40, DOI: 10.1039/c1cs15063d, Mar. 2011, pp. 4805-4839.

* cited by examiner

OPTICAL BASED GLUCOSE SENSOR

TECHNICAL FIELD

The disclosure generally relates to methods and devices for measuring an analyte present in a biological system, such as glucose levels in a patient.

BACKGROUND

Physiological characteristic sensors may be use in a variety of specialized applications. For example, implantable electrochemical sensors may be used in continuous glucose monitoring systems to facilitate treatment of diabetes, such as monitoring glucose levels overtime for adjusting a treatment regimen that includes regular administration of insulin to a patient. Typically, electrochemical sensors for continuous glucose monitoring include a distal segment positioned subcutaneously in direct contact with the interstitial fluid of a patient. Challenges in glucose monitoring with electrochemical sensor based systems, including wafer-scale systems, may include providing a suitable reference electrode, selection of suitable sensor chemistry, and work electrode longevity.

SUMMARY

In some examples, the medical device and technique described herein are configured to use an optical sensor to measure a concentration of one or more analytes in a biological system. The medical device may include the optical sensor and processing circuitry. The medical device may be implantable, such as insertable transcutaneously into the interstitial fluid or within a body cavity of a human patient. The optical sensor may be configured to detect a fluorescence emitted by a fluorophore in response to exposure to an analyte, and produce a signal indicative of the concentration of the analyte. The processing circuitry may retrieve, identify, and process the signal from the optical sensor to determine the concentration of the analyte. In this way, the medical device may enable continuous or near continuous monitoring of analyte concentrations in a biological system. The described optical sensors may have improved accuracy, longevity, and/or reliability compared to other sensors, including, for example, electrochemical sensors.

In some examples, the disclosure describes a medical device that includes an optical sensor including a light source configured to emit radiation; a reference optical beacon including a first fluorophore configured to absorb at least a portion of the radiation emitted by the light source and emit, based on a first concentration of a substance proximate the reference optical beacon, a first fluorescence; a test optical beacon that includes a reagent substrate configured to react with an analyte proximate the reagent substrate to modulate a concentration of the substance; and a second fluorophore configured to absorb at least a portion of the radiation emitted by the light source and emit, based on a second concentration of the substance proximate the second fluorophore, a second fluorescence; and a photodetector configured to detect the first fluorescence and the second fluorescence; and processing circuitry operatively coupled to the optical sensor, where the processing circuitry is configured to: receive, from the optical sensor, one or more signals indicative of the first fluorescence and the second fluorescence; and determine, based on the one or more signals, a difference between the first fluorescence and the second fluorescence, where the difference is indicative of a concentration of the analyte.

In some examples, the disclosure describes an optical sensor that includes a light source configured to emit radiation; a reference optical beacon including a first fluorophore configured to absorb at least a portion of the radiation emitted by the light source and emit, based on a first concentration of a substance proximate the reference optical beacon, a first fluorescence; and a test optical beacon including a reagent substrate configured to react with an analyte proximate the reagent substrate to modulate a concentration of the substance; and a second fluorophore configured to absorb at least a portion of the radiation emitted by the light source and emit, based on a second concentration of the substance proximate the second fluorophore, a second fluorescence; and a photodetector configured to detect the first fluorescence and the second fluorescence, where the concentration of the analyte is related to a difference between the first fluorescence and the second fluorescence.

In some examples, the disclosure describes a method that includes emitting, by a light source of an optical sensor, radiation; detecting, by a photodetector of the optical sensor, a first fluorescence emitted by a first fluorophore of a reference optical beacon of the optical sensor in response to absorption of the radiation emitted by the light source, where the first fluorescence is based on a first concentration of a substance proximate the reference optical beacon; detecting, by the photodetector, a second fluorescence emitted by a second fluorophore of a test optical beacon of the optical sensor in response to absorption of the radiation emitted by the light source, where the second fluorescence is based on a second concentration of the substance proximate the test optical beacon, where the test optical beacon that includes a reagent substrate configured to react with an analyte proximate the reagent substrate to modulate a concentration of the substance; and determining, by processing circuitry operatively coupled to the optical sensor, based on the first fluorescence and the second fluorescence, a concentration of the analyte.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

BRIEF DESCRIPTION OF THE DRAWINGS

The details of one or more examples of this disclosure are set forth in the accompanying drawings and the description below. Other features, objects, and advantages of this disclosure will be apparent from the description, drawings, and claims.

The details of one or more examples of this disclosure are set forth in the accompanying drawings and the description below. Other features, objects, and advantages of this disclosure will be apparent from the description and drawings, and from the claims.

DETAILED DESCRIPTION

A medical device may include an optical sensor, processing circuitry, an antenna, and a power source. The optical sensor may include one or more light sources and one or more optical beacons. For example, the one or more light source may include a plurality of light emitting diodes (LEDs) that are configured to emit radiation (e.g., light) having a selected wavelength range. The one or more optical beacons may include a reference optical beacon and a test (e.g., active) optical beacon. Both optical beacons include a fluorophore configured to interact with a substance present in a sample fluid to which the optical sensor is exposed. Additionally, the test optical beacon includes a reagent substrate. In some examples, an analyte in the sample fluid may react with the reagent substrate to modulate a concentration of the substance in a region proximate the test optical beacon and affect the fluorescence of the fluorophore. As used herein, the region proximate the optical beacon may include a region in which a substance is able to chemically interact with the fluorophore within a duration of time of the fluorescence decay of the fluorophore. Each optical beacon may include a photodetector configured to detect at least an intensity and duration of the fluorescence decay of the respective fluorophores. When exposed to the radiation emitted from the one or more light source, the fluorescence of the test optical beacon may be indicative of a concentration of the analyte. The reference optical beacon may be used to adjust for an ambient concentration of the substance. The respective fluorescence of the reference optical beacon and the test optical beacon may be used to generate a respective signals, which are received and processed by the processing circuitry to determine the concentration of the analyte.

The described medical devices and technique may include several advantages over other analyte detection systems and techniques. For example, the described medical devices and system may enable analyte detection without reference electrodes as used electrochemical sensors. Eliminating the need for a reference electrode may simplify device design. Additionally, or alternatively, the described medical devices and techniques may increase device longevity compared to other sensors, such as electrochemical sensors. For example, the described medical devices and techniques may utilize sensor chemistries that have a longer working life relative to electrochemical electrodes.

Figure 1A:
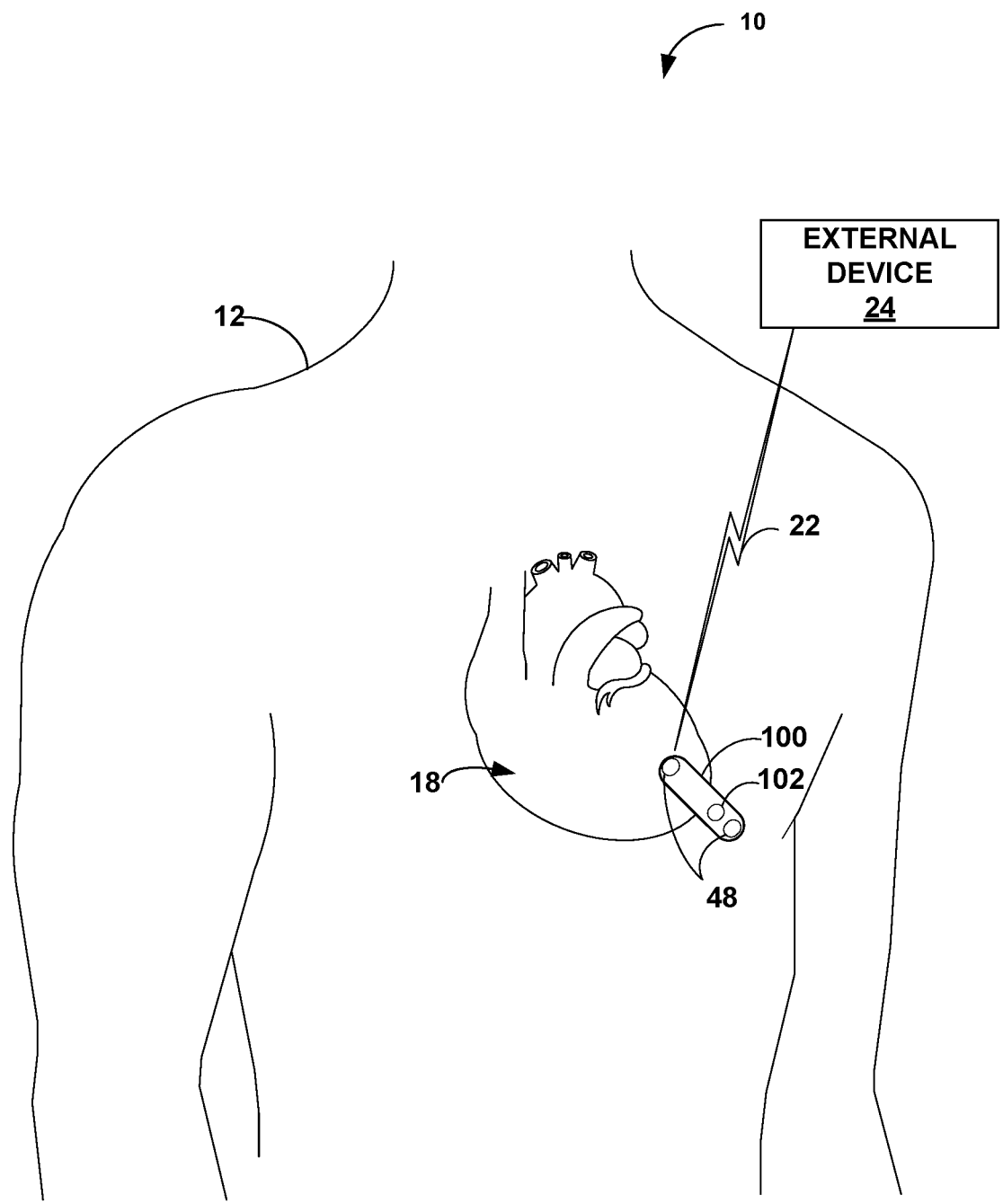
FIG. 1A is a conceptual drawing illustrating an example medical device in conjunction with a patient according to various examples described in this disclosure.

FIG. 1A is a conceptual drawing illustrating an example medical system 10 in conjunction with a patient 12 according to various examples described in this disclosure. The systems, devices, and methods described in this disclosure may include examples configurations of an optical sensor 102 located on and/or within medical device 100. For purposes of this description, knowledge of cardiovascular anatomy and functionality is presumed, and details are omitted except to the extent necessary or desirable to explain the context of the techniques of this disclosure. System 10 includes medical device 100 having optical sensor 102, implanted at or near the site of a heart 18 of a patient 12 and an optional external computing device 24.

Medical device 100 may be in wireless communication with at least one of external device 24 and other devices not pictured in FIG. 1. In some examples, medical device 100 is implanted outside of a thoracic cavity of patient 12 (e.g., subcutaneously in the pectoral location illustrated in FIG. 1). Medical device 100 may be positioned near the sternum near or just below the level of the heart of patient 12, e.g., at least partially within the cardiac silhouette. In some examples, medical device 100 includes a plurality of electrodes 48, and is configured to sense a cardiac electrogram (EGM) via the plurality of electrodes. In some examples, medical device 100 takes the form of the LINQ™ ICM, or another ICM similar to, e.g., a version or modification of, the LINQ™ ICM. Therefore, in some embodiments, medical device 100 may serve as a combination sensor device suitable for monitoring and/or facilitating treatment of multiple conditions. For example, in embodiments such as the LINQ™ embodiments described, the medical device 100 may serve as a combination of a glucose sensor and/an ECG or cardiac monitoring device that may be uniquely suited for monitoring patient comorbidities. Although described primarily in the context of examples in which medical device 100 is an ICM, in various examples, medical device 100 may represent a cardiac monitor, a defibrillator, a cardiac resynchronization pacer/defibrillator, a pacemaker, an implantable pressure sensor, a neurostimulator, or any other implantable or external medical device that may, for example, have appropriate access to an analyte.

External device 24 may be a computing device with a user interface, such as a display viewable by the user and an interface for providing input to external device 24 (i.e., a user input mechanism). In some examples, external device 24 may be a notebook computer, tablet computer, workstation, one or more servers, smartphone, smartwatch, smart injection pen (such as, for example the InPen™ device available from Companion Medical, Inc. and Medtronic MiniMed, Inc.), insulin pump (such as for example, any one of the MiniMed™ 630G System, MiniMed™ 670G System, or MiniMed™ 770G System available from Medtronic MiniMed, Inc.), personal digital assistant, or another computing device that may run an application that enables the computing device to interact with medical device 100. External device 24 is configured to communicate with medical device 100 and, optionally, another computing device (not illustrated in FIG. 1), via wireless communication. External device 24, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets (including but not limited to BLE), or other communication technologies operable at ranges greater than near-field communication technologies).

External device 24 may be used to configure operational parameters for medical device 100. External device 24 may be used to retrieve data from medical device 100. The retrieved data may include values of physiological parameters measured by medical device 100, indications of episodes of arrhythmia or other maladies detected by medical device 100, and physiological signals recorded by medical device 100. For example, external device 24 may retrieve analyte concentrations recorded by medical device 100, e.g., due to medical device 100 determining that a change in analyte concentration exceeded a predetermined magnitude, or that predetermined maximum or minimum analyte concentration threshold was exceeded, during the segment, or in response to a request to record the segment from patient 12 or another user. Additionally, or alternatively, external device 24 may retrieve analyte concentrations, cardiac EGM segments recorded by medical device 100, e.g., due to medical device 100 determining that an episode of arrhythmia or another malady occurred during the segment, or in response to a request to record the segment from patient 12 or another user. In some examples, one or more remote computing devices may interact with medical device 100 in a manner similar to external device 24, e.g., to program medical device 100 and/or retrieve data from medical device 100, via a network such as a cloud computing network suitable for storing and processing data for the benefit of patients and/or health care providers, such as, for example, the CareLink™ Diabetes therapy management system available from Medtronic MiniMed, Inc.

In various examples, medical device 100 may include one or more additional sensor circuits configured to sense a particular physiological or neurological parameter associated with patient 12, or may include a plurality of sensor circuits, which may be located at various and/or different positions relative to patient 12 and/or relative to each other, and may be configured to sense one or more physiological parameters associated with patient 12.

For example, medical device 100 may include a sensor operable to sense a body temperature of patient 12 in a location of the medical device 100, or at the location of the patient where a temperature sensor coupled by a lead to medical device 100 is located. In another example, medical device 100 may include a sensor configured to sense motion, such as steps taken by patient 12 and/or a position or a change of posture of patient 12. In various examples, medical device 100 may include a sensor that is configured to detect breaths taken by patient 12. In various examples, medical device 100 may include a sensor configured to detect heartbeats of patient 12. In various examples, medical device 100 may include a sensor that is configured to measure systemic blood pressure of patient 12.

In some examples, one or more of the sensors of medical device 100 may be implanted within patient 12, that is, implanted below at least the skin level of the patient. In some examples, one or more of the sensors of medical device 100 may be located externally to patient 12, for example as part of a cuff or as a wearable device, such as a device imbedded in clothing that is worn by patient 12. In various examples, medical device 100 may be configured to sense one or more physiological parameters associated with patient 12, and to transmit data corresponding to the sensed physiological parameter or parameters to external device 24, as represented by the lightning bolt 22 coupling medical device 100 to external device 24.

Transmission of data from medical device 100 to external device 24 in various examples may be performed via wireless transmission, using for example any of the formats for wireless communication described above. In various examples, medical device 100 may communicate wirelessly to an external device (e.g., an instrument or instruments) other than or in addition to external device 24, such as a transceiver or an access point that provides a wireless communication link between medical device 100 and a network. Examples of communication techniques used by any of the devices described herein may include radiofrequency (RF) telemetry, which may be an RF link established via Bluetooth®, BLE, Wi-Fi, or medical implant communication service (MICS).

In some examples, system 10 may include more or fewer components than depicted in FIG. 1. For example, in some examples, system 10 may include multiple additional implantable medical devices (IMDs), such as implantable pacemaker devices or other IMDs, implanted within patient 12. In these examples, medical device 100 may function as a hub device for the other IMDs. For example, the additional IMDs may be configured to communicate with the medical device 100, which would then communicate to the external device 24, such as a user's smartphone, via a low-energy telemetry protocol.

Figure 1B:
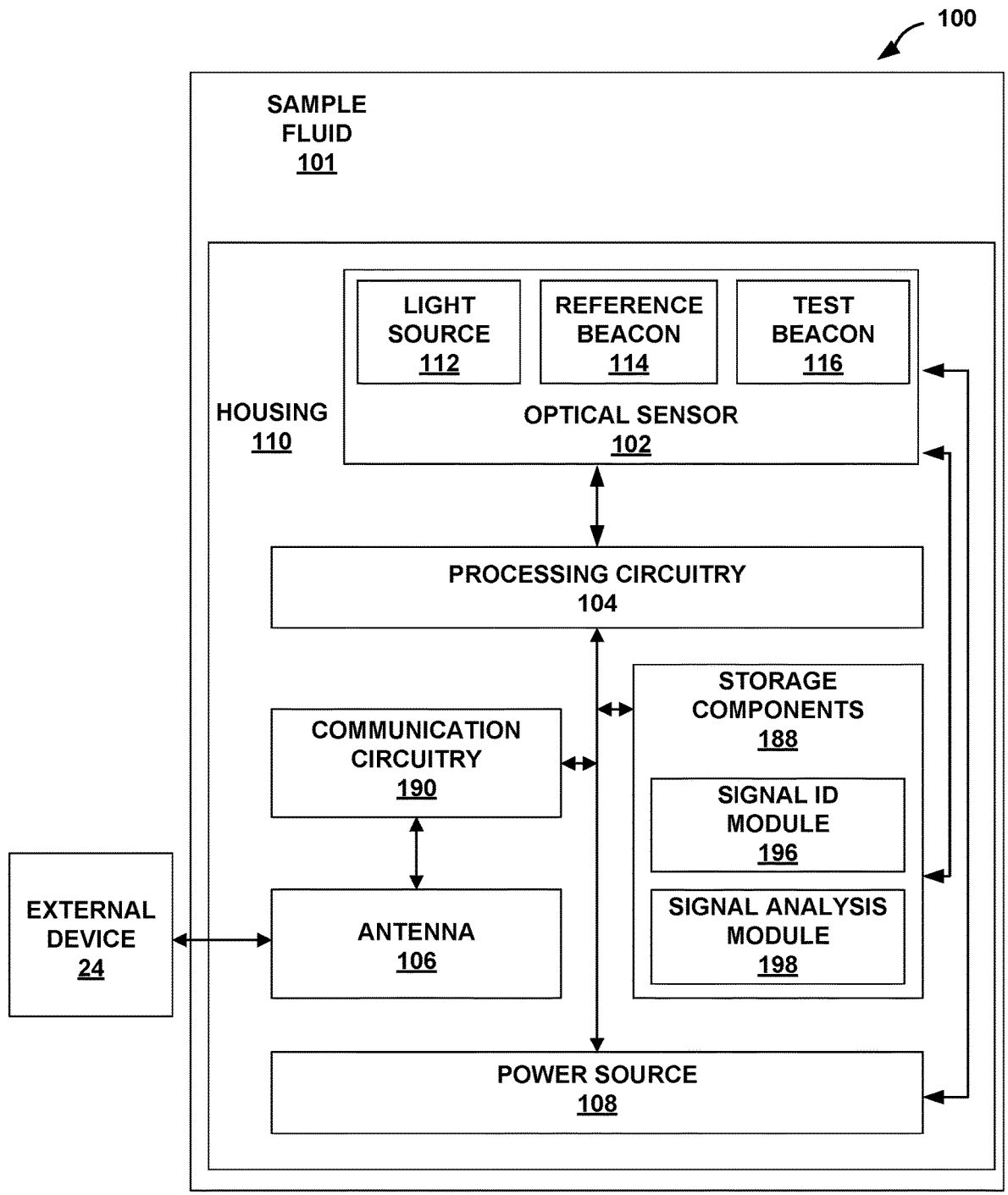
FIG. 1B is a schematic and conceptual diagram illustrating the example medical device, as illustrated in FIG. 1A, including an optical sensor.

FIG. 1B is a conceptual diagram illustrating a schematic and conceptual diagram of medical device 100 including optical sensor 102. In addition to the above described functionality, medical device 100 is configured to optically measure a concentration of one or more analytes in a sample fluid 101 of a biological system, such as a concentration of glucose of a human patient. Although described as detecting a concentration of glucose, in other examples, medical device 100 may be configured to measure of concentration of other analytes such as, for example, one or more of sodium, chloride, potassium, bicarbonate/carbon dioxide, blood urea nitrogen, creatinine, glucose, brain natriuretic peptide, C-reactive protein, troponin I, lactate, pH, or L-dopa. Sample fluid 101 may include, but is not limited to, one or more of blood, interstitial fluid, saliva, urine, spinal fluid, peritoneal fluid, or other bodily fluids.

Medical device 100 includes optical sensor assembly 102 (e.g., optical sensor 102), processing circuitry 104, an antenna 106, a power source 108, and housing 110. Medical device 100 may be insertable into a biological system. For example, medical device 100 may be transcutaneously insertable or implantable in interstitial fluid or a body cavity of a human patient. In other examples, a first portion of medical device 100 may be inserted into the skin, e.g., exposed to or otherwise in fluidly coupled to an interstitial fluid of the patient, and a second portion of the medical device may be affixed to or worn by the patient, e.g., as a skin worn patch. In this way, medical device 100 may enable continuous or near continuous monitoring of one or more analyte concentrations in the biological system.

Optical sensor 102 includes light source 112, reference optical beacon 114, and test optical beacon 116. Optical sensor 102 is configured to detect a fluorescence emitted by a fluorophore in response to exposure to an analyte, and produce a signal indicative of the concentration of the analyte.

Light source 112 includes one or more radiation sources configured to emit radiation having a selected wavelength range. For example, light source 112 may include one or more light emitting diodes (LEDs) or LASERs. In some examples, light source 112 may include two, three, four, five, or more LEDs arrange on an LED chip. Radiation emitted by light source 112 may include any suitable wavelength or range of wavelengths of radiation. In some examples, the radiation may include wavelengths in the visible range, e.g., within a range from about 380 nanometers (nm) to about 740 nm.

In some examples, light source 112 may emit radiation having a range of wavelengths selected based on an absorbance of a fluorophore of reference optical beacon 114 and/or test optical beacon 116. For example, the absorbance of the fluorophore may be substantially within a range from about 480 nm to about 700 nm. As used herein, absorbance substantially within a particular wavelength range may include a percentage of absorption within the range relative to a total absorption spectrum that is greater than 90%, such as greater than 95% or greater than about 99%. In such examples, light source 112 may have an emission spectrum substantially within a range from about 480 nm to about 700 nm. As used herein, an emission spectrum substantially within a particular wavelength range may include a percentage of emission within the range relative to a total emission spectrum that is greater than 90%, such as greater than 95% or greater than about 99%. As another example, the fluorophore may have a maximum absorbance peak of less than about 600 nm, such as about 590 nm. In such examples, light source 112 may have a peak emission wavelength of about 590 nm.

In examples in which light source 112 includes one or more LEDs with an emission wavelength greater than about 580 nm, light source 112 may include one or more LEDs driven by less than about 100 milliamps and/or a voltage within a range from about 1.5 volts (V) to about 2.5 V, such as from about 1.9 V to about 2.2 V. By driving light source 112 in the milliamp range, with less than about 2.5 V, and/or with an emission wavelength greater than about 580 nm, light source 112 may include a less complex circuit compared to an LED configured to emit light having a wavelength less than about 580 nm.

The radiation may be incident on a respective fluorophore of reference optical beacon 114 and test optical beacon 116. In response to the incident radiation, the respective fluorophore of reference optical beacon 114 and test optical beacon 116 may fluoresce. The respective fluorophores may include any suitable fluorophore. Example fluorophores include, but are not limited to, ruthenium-tris(4,7-diphenyl-1,10-phenanthroline) dichloride (Ru(dpp)), platinum(II) octaethylporphyrin (PtOEP), palladium(II) octaethylporphyrin (PdOEP), platinum(II)-5,10,15,20-tetrakis-(2,3,4,5,6-pentafluorphenyl)-porphyrin (PtTFPP), palladium(II)-5,10,15,20-tetrakis-(2,3,4,5,6-pentafluorphenyl)-porphyrin (PdTFPP), platinum(II) octaethylporphyrinketone (PtOEPK), palladium(II) octaethylporphyrinketone (PdOEPK), platinum(II) tetraphenyltetrabenzoporphyrin (PtTPTBP), palladium(II) tetraphenyltetrabenzoporphyrin (PtTPTBP), platinum(II) tetraphenyltetranaphthoporphyrin (PtPTPNP), or palladium(II) tetraphenyltetranaphthoporphyrin (PdPTPNP).

In some examples, a fluorophore may be selected to have a relatively higher light-emission efficiency, relatively higher brightness, and relatively longer emission time constant, compared to other fluorophores configured to interact with oxygen. In some examples, a fluorophore may be selected to fluoresce at a wavelength of about 580 nm or longer. In some examples, a fluorophore may be selected to have an emission wavelength within a range from about 600 nm to about 1100 nm and/or to match a peak sensitivity range for a silicon photodetector. In some examples, a fluorophore may be selected to be biocompatible and/or intrinsically stable for chronic use in vivo. The respective fluorophore of reference optical beacon 114 and test optical beacon 116 may have the same chemical composition or a different chemical composition.

The fluorophore may be configured to interact with a substance present in sample fluid 101 surrounding medical device 100. In some examples, the respective fluorophore of reference optical beacon 114 and test optical beacon 116 may be positioned on an external surface of housing 110 of medical device 100. In other examples, housing 110 may include one or more apertures fluidly coupling at least the respective fluorophore of reference optical beacon 114 and test optical beacon 116 to sample fluid 101. In these ways, the respective fluorophore of reference optical beacon 114 and test optical beacon 116 may be in contact with sample fluid 101.

In some examples, the fluorophore may interact with oxygen present in sample fluid 101. For example, a fluorescence of the respective fluorophores may be quenched by oxygen. In other words, a higher concentration of oxygen proximate test optical beacon 116 may cause the fluorophore of test optical beacon 116 to emit a lesser intensity of fluorescence compared to the fluorescence of the fluorophore of a reference optical beacon 114 that is proximate to a relatively lower concentration of oxygen. In this way, the fluorescence of the fluorophore of reference optical beacon 114 and test optical beacon 116 may be used to determine a variation in a concentration of the substance proximate each respective fluorophore.

For example, reference optical beacon 114 may be used to adjust for an ambient concentration of a substance, such as oxygen, in sample fluid 101, whereas test optical beacon 116 may include an additional chemistry configured to react with a selected analyte to change a concentration of the substance proximate to test optical beacon 116. In some examples, in addition to the fluorophore, test optical beacon 116 includes a reagent substrate configured to react with a selected analyte to change a concentration of the substance proximate to test optical beacon 116. The reagent substrate may include one or more enzymes, catalysts, antibodies, molecular imprinted polymers, aptamers, or other materials configured to react with an analyte to modulate a concentration of a selected substance.

In examples in which the analyte includes glucose, the reagent substrate may include glucose oxidase and catalase. For example, the glucose oxidase consumes oxygen (e.g., the substance) to oxidize glucose present in sample fluid 101 to yield gluconic acid and hydrogen peroxide (e.g., a bi-product). The catalase reduces the hydrogen peroxide to yield water and oxygen (e.g., the substance). By consuming the hydrogen peroxide, catalase may reduce or prevent inhibition of glucose oxidase by the hydrogen peroxide. By consuming oxygen via glucose oxidase and producing oxygen via catalase, the reagent substrate is configured to modulate a local oxygen concentration that is indicative of the concentration of glucose.

In some examples, reference optical beacon 114 and/or test optical beacon 116 may include limiting membrane and/or a selective ion transfer membrane disposed on the fluorophore and/or the reagent substrate. The membrane may be selectively permeable to the analyte. For example, the membrane may control a rate of diffusion of the analyte from sample fluid 101 to a reagent substrate of test optical beacon 116. In this way, the membrane may control an extent of reaction or a rate of reaction of the analyte at a surface of the reagent substrate, e.g., by controlling a rate of exposure of the reagent substrate to the analyte. Additionally, or alternatively, the membrane may extend a linear range of a respective optical beacon, e.g., relative to a glucose concentration in the sample fluid 101, by limiting a permeability of glucose. In other words, the membrane may prevent saturation of the reagent substrate (e.g., enzymes of the reagent substrate) over a greater range of glucose concentrations relative to an optical beacon without a reagent substrate. In this way, the chemistry of the fluorophore, reagent substrate, and/or membrane may be selected to be specific to the analyte, extend a linear range of the respective optical beacon, and/or increase a useable life of the respective optical beacon.

Reference optical beacon 114 and test optical beacon 116 each include a respective photoreceptor in line-of-sight with the respective fluorophore. The respective photodetector of reference optical beacon 114 and test optical beacon 116 are configured to detect a respective intensity of the respective fluorescence of the fluorophore for each of reference optical beacon 114 and test optical beacon 116. Although described as including two photodetectors, in some examples, optical sensor 102 may include a single photodetector, each of reference optical beacon 114 and test optical beacon 116 being disposed on a portion of the single photodetector. The respective photodetectors may include any suitable photodetector. In some examples, the photodetectors may include flip-chip photodetectors. The respective photodetectors may be selected to detect a wavelength or a range of wavelengths of radiation emitted by the respective fluorophore of reference optical beacon 114 and test optical beacon 116. For example, in response to radiation emitted from light source 112 incident on the fluorophore, the fluorophore may have an emission spectrum substantially within a range from about 700 nm to about 820 nm, and/or a maximum emission peak of about 760 nm. In such examples, the photodetector may be configured to detect radiation within a range from about 380 nm to about 1100 nm, such as within a range from about 700 nm to about 820 nm, and/or with a peak detection sensitivity of within a range from about 700 nm to about 820 nm. In some examples, the peak detection sensitivity may be an intrinsic property of the photodetector, e.g., based on materials of construction and/or physical configuration. In some examples, the detection range or peak detection sensitivity of the photodetector may be modulated by, for example, one or more filters, such as a bandpass filter, a light absorbing gel or film, or other discrete filter between a fluorophore and a respective photodetector. Filtering may, for example, enable a photodetector to detect a fluorescence of a fluorophore, while substantially not detecting light emitted by a light source.

The respective photodetectors may transmit a signal indicative of the respective intensity to processing circuitry 104. Processing circuitry 104 may include various types of hardware, including, but not limited to, microprocessors, controllers, digital signal processors (DSPs), application specific integrated circuits (ASICs), field-programmable gate arrays (FPGAs), or equivalent discrete or integrated logic circuitry, as well as combinations of such components. The term "processing circuitry" may generally refer to any of the foregoing logic circuitry, alone or in combination with other logic circuitry, or any other equivalent circuitry. In some examples, processing circuitry 104 may represent and/or include additional components. Processing circuitry 104 represents hardware that can be configured to implement firmware and/or software that sets forth one or more of the algorithms described herein. For example, processing circuitry 104 may be configured to implement functionality, process instructions, or both for execution of processing instructions stored within one or more storage components 188, such as signal identification module 196 and/or signal analysis module 198.

One or more storage components 188 may be configured to store information within medical device 100. One or more storage components 188, in some examples, include a computer-readable storage medium or computer-readable storage device. In some examples, one or more storage components 188 include a temporary memory, meaning that a primary purpose of one or more storage components 188 is not long-term storage. One or more storage components 188, in some examples, include a volatile memory, meaning that one or more storage components 188 does not maintain stored contents when power is not provided to one or more storage components 188. Examples of volatile memories include random access memories (RAM), dynamic random-access memories (DRAM), static random-access memories (SRAM), and other forms of volatile memories known in the art. In some examples, one or more storage components 188 are used to store program instructions for execution by processing circuitry 104. One or more storage components 188, in some examples, are used by software or applications running on processing circuitry 104 to temporarily store information during program execution.

In some examples, one or more storage components 188 may be configured for longer-term storage of information. In some examples, one or more storage components 188 may include non-volatile storage elements. Examples of such non-volatile storage elements include flash memories, or forms of electrically programmable memories (EPROM) or electrically erasable and programmable memories (EEPROM).

Processing circuitry 104, e.g., signal identification module 196, may be configured to identify a respective signal corresponding to a respective optical beacon. For example, signal identification module 196 may include a multiplexer configured to select between inputs from reference optical beacon 114 and test optical beacon 116. In some examples, input selection maybe based on a timing of light emitted by light source 112. For example, in response to a first light pulse emitted from light source 112, processing circuitry 104, e.g., signal identification module 196, may select an input from reference optical beacon 114 that is then output to processing circuitry 104 and/or signal analysis module 198 for processing. In response to a second light pulse emitted from light source 112 that is separated in time from the first light pulse, processing circuitry 104, e.g., signal identification module 196, may select an input from test optical beacon 116 that is then output to processing circuitry 104 and/or signal analysis module 198 for processing. In some examples, a duration between the first light pulse and the second light pulse may be greater than 1 millisecond, greater than 10 milliseconds, greater than 100 milliseconds, greater than one second, or more. For example, the duration between the first light pulse and the second light pulse may be based on a duration of fluorescence of the respective fluorophore in response to the first light pulse.

Processing circuitry 104, e.g., via signal analysis module 198, may be configured to process the identified signal to determine a concentration of an analyte. In some examples, signal analysis module 198 may be coupled to one or more capacitors configured to receive from a respective photodetector of reference optical beacon 114 or test optical beacon 116 a respective amount of electrical energy indicative of a fluorescence emission from a respective fluorophore. Processing circuitry 104, e.g., signal analysis module 198, may determine a difference between a first amount of electrical energy associated with a fluorescent decay of the fluorophore of reference optical beacon 114 and a second amount of electrical energy associated with a fluorescent decay of the fluorophore of test optical beacon 116. The fluorescent decay of the respective fluorophores may include substantially all fluorescence emitted by the respective fluorophore in response to incident light emitted by light source 112, such as at least 80%, at least 90%, at least 95%, or at least 99% of a total fluorescent decay of the respective fluorophore. By using a capacitor to store electrical energy from the respective photodetectors in response to the fluorescent decay of the respective fluorophore, the amount electrical energy may more accurately represent the fluorescent decay compared to other methods, such as time dependent sampling of the fluorescence of the respective fluorophore. Additionally, or alternatively, using a capacitor to store electrical energy indicative of the fluorescent decay may simplify circuitry design relative to other methods, such as time dependent sampling of the fluorescence of the respective fluorophore.

Each of signal identification module 196 and signal analysis module 198 may be implemented in various ways. For example, one or more of signal identification module 196 and signal analysis module 198 may be implemented as an application or a part of an application executed by processing circuitry 104. In some examples, one or more of signal identification module 196 and signal analysis module 198 may be implemented as part of a hardware unit of medical device 100 (e.g., as circuitry). In some examples, one or more of signal identification module 196 and signal analysis module 198 may be implemented remotely on external device 24, for example, as part of an application executed by one or more processors of external device 24 or as a hardware unit of external device 24. Functions performed by one or more of signal identification module 196 and signal analysis module 198 are explained below with reference to the example flow diagram illustrated in FIG. 8.

Processing circuitry 104 may be configured to communicate, via antenna 106, with one or more external devices 24. For example, medical device 100 may include communications circuitry 190 operatively coupled to processing circuitry 104. Communications circuitry may be configured to send and receive signals to enable communication with an external device 24 via antenna 106. Communications circuitry 190 may include a communications interface, such as a radio frequency transmitter and/or receiver, cellular transmitter and/or receiver, a Bluetooth® interface card, or any other type of device that can send information or send and receive information. In some examples, the communications interface of communications circuitry 190 may be configured to send and/or receive data via antenna 106. In some examples, medical device 100 uses communications circuitry 190 to wirelessly transmit (e.g., a one-way communication) data to external device 24. In some examples, external devices 24 may include, but is not limited to, a radio frequency identification reader, a mobile device, such as a cell phone or tablet, or a computing device operatively coupled to an electronic medical records database or remote server system. In this way, antenna 106 may be operatively coupled to the processing circuitry and configured to transmit data representative of the concentration of the analyte to external device 24.

Medical device 100 includes antenna 106 operatively coupled to processing circuitry 104 to enable medical device 100 to communicate to an external device 24, e.g., while operating completely within a biological system. In some examples, processing circuitry 104 may cause communication circuitry 190 to transmit, via antenna 106, data indicative of a determined concentration of an analyte, such as processed data, unprocessed signals from optical sensor 184, or both. In some examples, external device 24 may continuously or periodically interrogate or poll communications circuitry 190 via antenna 106 to cause processing circuitry 104 to receive, identify, or process signals from optical sensor 184. By receiving, identifying, or processing signals from optical sensor 184 only when interrogated or polled by external device 24, processing circuitry may conserve power or processing resources.

Medical device includes power source 108 to enable medical device 100 to operate completely within the biological system. Power source 108 may be operatively coupled to optical sensor 102 (e.g., light source 112), processing circuitry 104, storage components 188, and/or communication circuitry 190. In some examples, power source 108 may be operatively coupled to optical sensor 102 to one or more LEDs of light source 112. Power source 108 may include any suitable power source, such as, for example, primary cell, a secondary cell, a solid state battery, a lithium ion battery, a lithium ion micro battery, a fuel cell, or combinations thereof.

By using power source 108 to power the components of medical device 100 and antenna 106 to communicate with one or more external devices 24, medical device 100 may be configured to enable chronic, continuous, and/or substantially continuous monitoring of the analyte concentration in the biological system.

Medical device 100 includes housing 110 that is configured to protect components of medical device 100 from the environment of the biological system. Housing 110 may be formed to separate at least a portion of one or more of optical sensor 102, processing circuitry 104, an antenna 106, and/or a power source 108 from the environment surrounding medical device 100. In some examples, housing 110 may include one or more biocompatible materials coating or encasing the components of medical device 100. One or more components of medical device 100, such as portions of optical sensor 102 or power source 108 may be disposed outside housing 110, such as, for example, affixed to an external surface of housing 110 or defining an external surface of medical device 100. As one example, antenna 106 may be affixed to an external surface of housing 110 to improve transmission properties of antenna 106. Housing 110 may include any suitable shape, such as rectilinear or curvilinear. In some examples, housing 110 may be shaped to facilitate insertion of medical device 100 into a body cavity of a human patient. For example, housing 110 may include a cylindrical shape to be loaded into an insertion tool or include rounded corners and edges to reduce irritation to the patient.

Housing 110 may be any suitable dimensions. In some examples, a height of housing 110 may be between approximately 1 millimeter (mm) and approximately 8 mm, such as approximately 4 mm. In some examples, a width of housing 110 may be between approximately 5 mm and approximately 15 mm, such as approximately 7 mm. In some examples, a length of the housing 182 may be between approximately 20 mm and approximately 60 mm, such as approximately 45 mm. In some examples, the components of medical device 100 may be layered or stacked inside housing 110 to reduce the size of medical device 100 compared to a device in which the components are not layered or stacked.

In some examples, the components of medical device 100 may be arranged to facilitate operation of the components.

Figure 2:
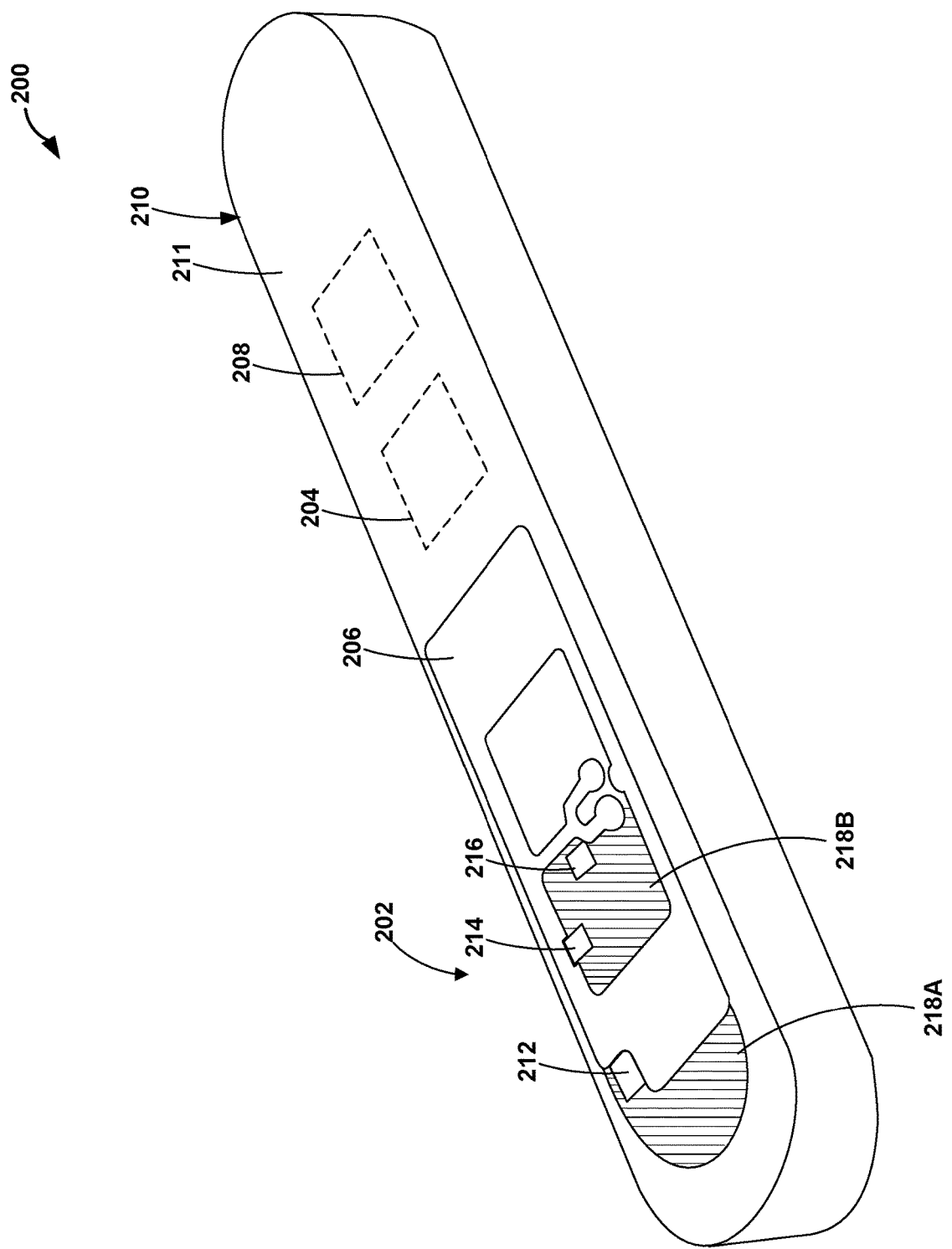
FIG. 2 is a conceptual diagram illustrating a perspective view of an example medical device including an optical sensor.

FIG. 2 is a conceptual diagram illustrating a perspective view of an example medical device 200 including an optical sensor 202. Medical device 200 may be the same or substantially similar to medical device 100 discussed above in reference to FIG. 1. For example, medical device 200 may include optical sensor 202 including light source 212, reference optical beacon 214, and test optical beacon 216?, processing circuitry 204, antenna 206, power source 208, and housing 210, which may be the same or substantially similar to the similarly numbered features discussed above in reference to medical device 100 illustrated in FIGS. 1A and 1B.

As illustrated in FIG. 2, antenna 206 is disposed on an exterior surface 211 of housing 210. In some examples, antenna 206 may include a substrate layer and a metalized layer formed on the substrate layer. The substrate layer may include, for example, biocompatible polymer, such as polyamide or polyimide, silica glass, silicon, sapphire, or the like. The metalized layer may include, for example, aluminum, copper, silver, or other conductive metals. Antenna 206 may include other materials, such as, for example, ceramics or other dielectrics (e.g., as in dielectric resonator antennas). In some examples, antenna 206, e.g., a metalized layer or the like, may be formed directly on exterior surface 211 of housing 210.

Regardless of the material, antenna 206 may include an opaque or substantially opaque material. For example, an opaque (e.g., or substantially opaque) material may block transmission of at least a portion of radiation of a selected wavelength, such as, between about 75% and about 100% of visible light.

In examples in which antenna 206 includes an opaque material, components of optical sensor 202 may be arranged relative to portions of antenna 206 to reduce or prevent optical interference between components. For example, as illustrated in FIG. 2, light source 212 is positioned on an outer perimeter of antenna 206, whereas reference optical beacon 214 and test optical beacons 216 are positioned within an aperture defined by antenna 206. In this way, antenna 206 may define an optical boundary of opaque material that reduces or prevents transmission of light from light source directly to a respective photodetector of reference optical beacon 214 and test optical beacons 216. Rather, light emitted from light source 212 must travel through an environment external to medical device 200. In this way, the emitted light may be incident only on the fluorophore of reference optical beacon 214 and the fluorophore and/or reactive substrate of test optical beacon 216. Hence, the optical signal generated by the respective photodetector of reference optical beacon 214 and test optical beacon 216 is produced substantially only by fluorescence of the respective fluorophores. Being produced substantially only by fluorescence of the respective fluorophores may exclude ambient radiation, fluorescence emitted by adjacent fluorophores, or light transmitted from light source 212 through components (e.g., a substrate) of medical device 200 to the respective photodetectors.

Although not illustrated in FIG. 2, in some examples, reference optical beacon 214 and test optical beacon 216 may be disposed on opposing portions of antenna 206. Disposing reference optical beacon 214 and test optical beacon 216 on opposing portions of antenna 206 may reduce or prevent fluorescence emitted by a respective fluorophore of reference optical beacon 214 and test optical beacon 216 from being detected by the respective photodetector of the other of reference optical beacon 214 and test optical beacon 216.

Additionally, or alternatively, medical device 200 may include optional optical masks 218A and 218B (collectively, optical mask 218). Optical mask 218 may be configured to reduce or prevent transmission of radiation out of or into a substrate of medical device 200. For example, as discussed above in reference to FIG. 1, a substrate of medical device 200 may include one or more transparent (e.g., or semi-transparent) materials, such as glass or sapphire. Portions of optical sensor 202, such as light source 212 and/or respective photodetectors of reference optical beacon 214 and test optical beacon 216 may be disposed within (e.g., under) the transparent material, relative to the environment surrounding medical device 200.

Light emitted from light source 112 may travel through the transparent material into the environment surrounding medical device 200. In some examples, at least a portion of the light may be incident on the transparent material at an angle that causes reflection or total internal reflection of the portion of light. Additionally, or alternatively, in examples in which medical device 200 is implanted in a patient, the tissue or biological material surrounding medical device 200 may cause diffuse scattering of the light. At least a portion of the scattered light may be incident on the transparent material at an angle causing total internal reflection of the portion of scattered light. Optical mask 218 may be disposed on an interior surface and/or an exterior surface of the transparent material to reduce or prevent reflection and/or total internal reflection of the light. In this way, optical mask 218 may reduce or prevent stray light from being transmitted through the transparent substrate to respective photodetectors of reference optical beacon 114 and test optical beacon 116.

The optional optical mask 218 may include a material configured to substantially absorb radiation emitted by light source 212. In some examples, optical mask 218 may include titanium nitride, columnar titanium nitride, titanium, or another material suitable to absorb selected wavelengths of radiation that may be emitted by light source 212.

Figure 3:
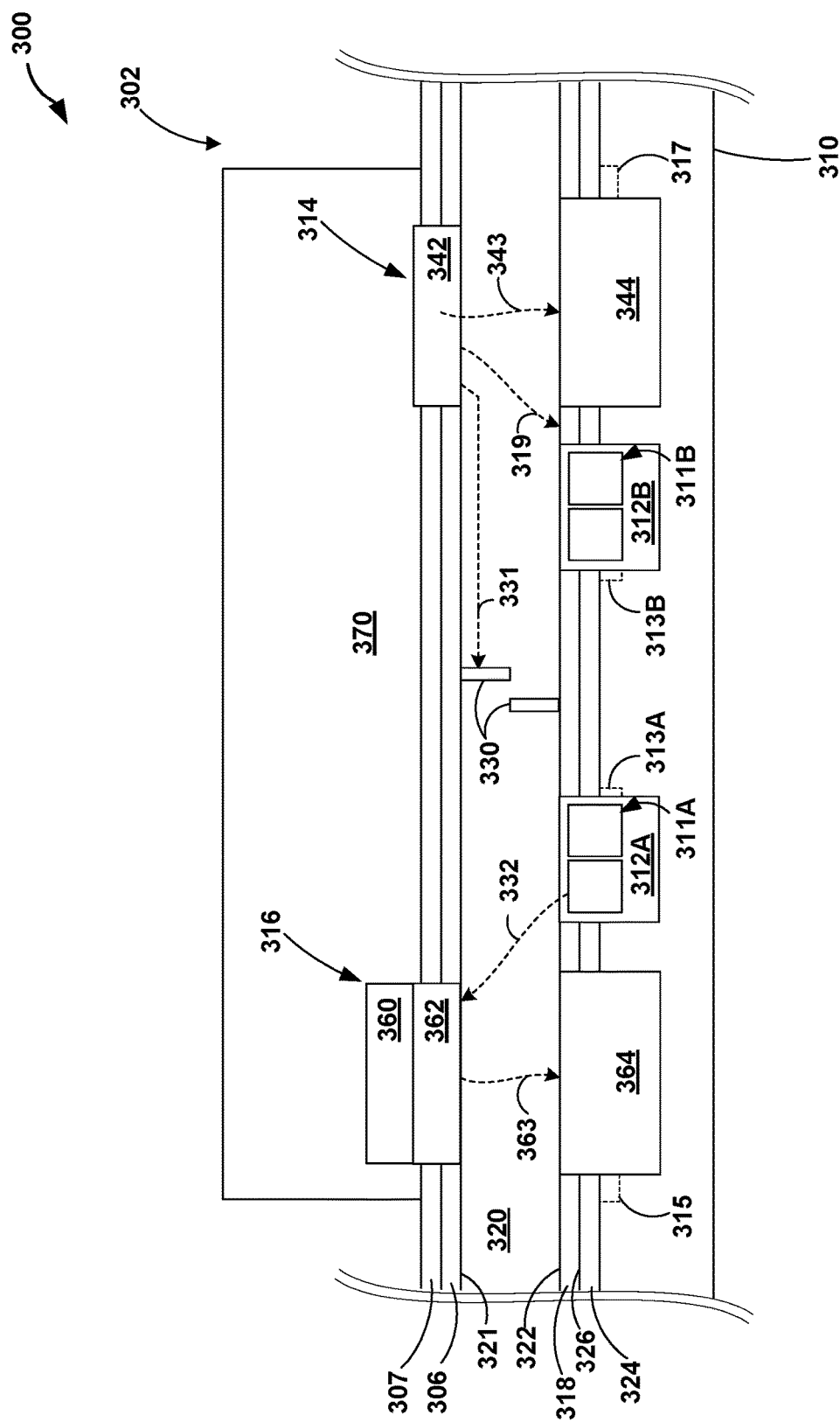
FIG. 3 is a conceptual diagram illustrating a partial cross-sectional side view of an example medical device including an optical sensor.

FIG. 3 is a conceptual diagram illustrating a partial cross-sectional side view of an example medical device 300 including an optical sensor 302. Medical device 300 may be the same or substantially similar to medical device 100 and/or medical device 200 discussed above in reference to FIGS. 1 and 2. For example, optical sensor 302 may include light sources 312A and 312B (collectively, light sources 312), reference optical beacon 314, test optical beacon 316, and antenna 306, and may be optatively coupled to processing circuitry and a power source (not illustrated), and may be encased in housing 310, which may be the same or substantially similar to the similarly numbered features discussed above in reference to medical device 100 and/or medical device 200 illustrated in FIGS. 1A, 1B, and 2.

Optical sensor 302 may include any suitable arrangement of light sources 312, reference optical beacon 314, and test optical beacon 316. As illustrated in FIG. 3, medical device 300 includes a substrate layer 320 defining surfaces 321 and 322. In some examples, substrate layer 320 may include sapphire, a sapphire wafer, silica glass, a glass wafer, silicon, a biocompatible polymer, polyamide, polyimide, a liquid crystal polymer, or a dielectric material. In some examples, surfaces 321 and/or 322 are substantially planar. In other examples, surfaces 321 and/or 322 may define surface features, such as ridges, valleys, or apertures, corresponding to features such as at least a portion of light sources 312, reference optical beacon 314, and test optical beacon 316, electrical traces, through vias, light blocking regions, or the like. Surface features on or in surfaces 321 and/or 322 may be formed by any suitable means, such as, for example, machining, laser etching, chemical etching, or semiconductor manufacturing techniques such as front-end-of-line (FEOL) processes. In this way, substrate layer 320 may be formed to support additional layers, facilitate manufacture of the medical device 300, or both.

An optical mask 318 may be disposed on at least a portion of surface 322 or, in some examples, a portion of surface 321. As discussed above in reference to FIG. 2, optical mask 318 is configured to reduce or prevent transmission of radiation out of or into substrate layer 320 of medical device 200. For example, optical mask 318 may absorb radiation, such as light ray 319, incident on optical mask 318.

An interconnect layer 324 may be disposed on surface 326 of optical mask 318. Interconnect layer 324 is configured to electrically couple light sources 312, reference optical beacon 314, and test optical beacon 316 to processing circuitry and/or a power source of medical device 300. For example, light sources 312, reference optical beacon 314, and test optical beacon 316 may be electrically coupled to interconnect layer 324 by respective electrical traces 313A, 313B, 315, and 317.

Interconnect layer 324 may include an electrically conductive material, such as, for example, aluminum, cadmium, chromium, copper, gold, nickel, platinum, titanium, indium nitride, indium phosphide, zinc oxide, alloys thereof, or the like. In some examples, surface 322 may be metallized by, for example, chemical vapor deposition, physical vapor deposition, thermal spraying, cold spraying, or the like, to form interconnect layer 324. In some examples, interconnect layer 324 may form a plurality of electrical traces, e.g., formed using semiconductor manufacturing techniques such as back-end-of-line (BEOL) processes. A respective electrical trace or the plurality of electrical traces may electrically couple one or more components of medical device 300.

Although illustrated as embedded or partially embedded in optical mask 318 and interconnect layer 324, in some examples, one or more portions of light sources 312, reference optical beacon 314, and test optical beacon 316 may be formed on a portion of optical mask 318 and/or interconnect layer 324. For example, light sources 312 may be positioned on and electrically coupled to a surface of optical mask 318 and/or interconnect layer 324, where optical mask 318 and interconnect layer 324 may define an aperture optically coupling light sources 312 to substrate 320. Each of reference optical beacon 314 and test optical beacon 316 may be similarly positioned on a surface of optical mask 318 and/or interconnect layer 324.

In some examples, medical device 300 may include one or more optical barriers 330 extending at least partially through substrate layer 320. For example, optical barrier 330 may extend through at least a portion of substrate layer 320. Optical barriers 330 may extend through only a portion of substrate layer 320 to enable substrate layer 320 to define a hermetic seal between an interior and exterior of medical device 300. Optical barrier 330 may be substantially the same as or similar to optical mask 318, except that optical barrier 330 may extend into substrate layer 320. For example, optical barrier 330 may include a material configured to absorb at least a portion of radiation transmitted through substrate layer 320. In some examples, radiation, such as light ray 331, may be incident on an interface between fluorophore 324 and substrate layer 320 at an angle that results in total internal reflection of the radiation. By orienting optical barrier 330 between components of optical sensor 302, optical barrier may substantially reduce or prevent light ray 331 from reaching photodetector 364 of test optical beacon 316. In this way, one or more optical barriers 330 may be disposed between reference optical beacon 314 and test optical beacon 316 to reduce or prevent fluorescence emitted from either reference optical beacon 314 and test optical beacon 316 from reaching the other of reference optical beacon 314 and test optical beacon 316.

In operation, when light is emitted from light source 312A, e.g., by LEDs 311A, the light, e.g., light ray 332, may travel through a portion of substrate layer 320 and may be incident on test optical beacon 316. When light is emitted from light source 312B, e.g., by LEDs 311B, the light may travel through a portion of substrate layer 320 and may be incident on test optical beacon 314.

Reference optical beacon 314 includes a fluorophore 342 and a photodetector 344. At least a portion of radiation emitted by light source 312B is incident on fluorophore 342. Fluorophore 342 absorbs at least a portion of the radiation, and emits a fluorescence 343 that is incident on photodetector 344. Fluorophore 342 is exposed to the environment surrounding medical device 300. In some examples, as discussed above, the fluorescence 343 of fluorophore 342 in response to incident radiation is associated with a concentration of substance present in the environment surrounding medical device 300. For example, fluorescence 343 may be quenched, e.g., reduced, proportional to a concentration of oxygen proximate fluorophore 342.

Test optical beacon 316 includes a reagent substrate 360, a fluorophore 362, and a photodetector 364. At least a portion of radiation, e.g., light ray 332, emitted by light source 312A is incident on fluorophore 362. Fluorophore 362 absorbs at least a portion of the incident radiation, and emits a fluorescence 363 that is incident on photodetector 364. Fluorophore 362 is exposed to reagent substrate 360. Reagent substrate 360, and in some examples at least a portion of fluorophore 362, is exposed to the environment surrounding medical device 300. Although illustrated as distinct layers, in some examples, reagent substrate 360 and fluorophore 362 may define a single layer, such as a layer composing a homogeneous mixture, heterogeneous mixture, or composite of reagent substrate 360 and fluorophore 362.

As discussed above in reference to FIG. 1, reagent substrate 360 may be configured to react with an analyte present in the proximate environment to modulate the concentration of the substance that interacts with fluorophore 362. In some examples, reagent substrate 360 includes an immobilization substrate configured to immobilize a reagent. As discussed above, the reagent may include at least one enzyme, catalyst, or other material configured to react with the analyte to yield the substance. In examples in which the analyte include glucose and the substance includes oxygen, the reagent may include an oxidase enzyme, such as glucose oxidase. In some examples, the reagent may be immobilized on an immobilization substrate by, for example, physical entrapment (e.g., a respective reagent physically unable to pass through pores of the immobilization substrate), chemical bonding (e.g., ionic bonding, covalent bonding, van der Waals forces, and the like), or combinations thereof. In some examples, the immobilization substrate may include a polymer, such as polylysine, aminosilane, epoxysilane, or nitrocellulose, or a substrate having a three-dimensional lattice structure, such as a hydrogel, an organogel, or a xerogel. In some examples, the immobilization substrate may include a ligand configured to chemically bond to at least a portion of a respective reagent. For example, the immobilization substrate including glutaraldehyde may immobilize glucose oxidase. A respective immobilization substrate including primary amine conjugation enniatin may immobilize (used for sodium Na+ detection) can be immobilized to the working electrode through. In some examples, the immobilization substrate may include, but is not limited to, glutaraldehyde, thiol based conjugation compounds (e.g., 16-mercaptohexadecanoic acid (MHDA), diethyldithiocarbamic acid (DSH), dithiobissuccinimidylundecanoate (DSU), purine conjugation compounds, streptavidin-biotin conjugation compounds, a primary amine and a vinyl pyridine polymer, lysine, 1-ethyl-3-(3-dimethylaminopropyl)carbodiimide hydrochloride (EDC) and N-hydroxysuccinimide (NHS) coupling, agarose based gel and polymer mixtures, silane crosslinker, (hydroxyethyl)methacrylate, and poly(ethylene glycol) diacrylate polymer. In some examples, the immobilization substrate may be transparent or semi-transparent to enable radiation, e.g., light rays 332B, to reach fluorophore 362. By immobilizing a reagent, the immobilization substrate may reduce loss of the reagent to the sample fluid.

In examples in which reagent substrate 360 includes at least one enzyme, the at least one enzyme may be selected based on the analyte to be detected. For example, the at least one enzyme may be selected from the group consisting of glucose oxidase, lactate oxidase, catalase, or mixtures thereof. In some examples, the at least one enzyme may be selected to react with a selected analyte and provide a reaction pathway to enable detection of the concentration of the selected analyte. For example, fluorescence 343 may be quenched, e.g., reduced, proportional to a concentration of oxygen proximate fluorophore 342. In examples in which reagent substrate 360 includes glucose oxidase (e.g., notatin), glucose oxidase may oxidize glucose in the sample fluid to produce D-glucono-δ-lactone and hydrogen peroxide. The hydrogen peroxide may be reduced by catalase to produce oxygen. This modulation in the oxygen concentration may be indicative of the glucose concentration in the sample fluid. In examples in which reagent substrate 360 includes lactate oxidase, lactate oxidase may oxidize lactic acid in the sample fluid to produce pyruvate and hydrogen peroxide. The hydrogen peroxide may be reduced by catalase to produce oxygen. This modulation in the oxygen concentration may be indicative of the lactic acid concentration in the sample fluid.

In some examples, reference optical beacon 314 and/or test optical beacon 316 may include one or more permeable membranes 370. Membrane 370 may be permeable to at least the analyte and, in some examples, configured to block interfering cellular bodies or molecules from binding or adhering to a respective constituents of reference optical beacon 314 and/or test optical beacon 316. For example, a glucose membrane may block large cellular bodies or molecules, such as red blood cells, white blood cells, acetaminophen, ascorbic acid, and the like. Membrane 370 may include, for example, one or more limiting membranes, one or more selective ion transfer membranes, one or more ionophore membranes, or combinations thereof. Limiting membranes may include, but are not limited to, polyurethane polyurea block copolymer including a mixture of materials, such as, e.g., hexamethylene, diisocyanate, aminopropyl-terminated siloxane polymer, and polyethylene glycol, or a vinyl pyridine-styrene copolymer mixed with epoxy groups and coated with polyethylene glycol. Selective ion transfer membranes may include a porous material having a net positive (or negative) charge to enabling permeation of ions having a like charge through the selective ion transfer membrane, while reducing permeation of ion having an opposite charge. Selective ion transfer membranes may include, but are not limited to, amino methylated polystyrene salicylaldehyde, dibenzo-18-crown-6, cezomycin, enniatin, gramicidin A, lasalocid, macrolides, monensin, narasin, nigericin, nigericin sodium salt, nonactin, polyimide/lycra blend, salinomycin, valinomycin, or mixtures thereof. Ionophore membranes may include a plurality of ionophores dispersed in an ionophore matrix material, where the plurality of ionophores may be selected to be preferentially permeable to a selected ion or group of ions. The ionophores may include, but are not limited to, crown ethers, cryptands, calixarenesm, phenols, amino methylated polystyrene salicylaldehyde, beauvericin, calcimycine, cezomycin, carbonyl cyanide m-chlorophenyl hydrazone, dibenzo-18-crown-6, enniatin, gramicidin A, ionomycin, lasalocid, macrolides, monensin, nigericin, nigericin sodium salt, narasin, nonactin, polyimide/lycra blend, salinomycin, tetronasin, valinomycin, potassium ionophore III (BME 44) or mixtures thereof. Ionophore matrix material may include, but is not limited to, polyvinylchloride, silicone, fluorosilicone, polyurethane, glutaraldehyde, UV curable polymers like PVA-SbQ, PVA hydrogels, pHEMA-HAA crosslinking, and agarose gel. In this way, the optical beacons may be configured to react with a selected analyte or a derivative thereof to produce a response signal to the presence of the selected analyte.

In some examples, one or more regions of membrane 370 may include a light absorbent material. For example, membrane 370 may include, in addition to the one or more above described limiting membranes, light absorptive material, a pigment, or a dye configured to at least partially absorb radiation incident on membrane 370. In some examples, the light absorbing region of membrane 370 may include a portion of membrane 370 disposed between optical beacons 314 and 316. In this way, membrane 370 may be configured to reduce transmission of radiation between fluorophores 342 and 362. Additionally, or alternatively, the light absorbing region of membrane 370 may include the entire volume or at least a total surface area of membrane 370. In this way, membrane 370 may substantially block ambient light incident on optical beacons 314 and 316.

Antenna 306 may be disposed on surface 321 of substrate layer 320. In some examples, antenna 306 may define an optical boundary of opaque material that reduces or prevents transmission of light between fluorophores 342 and 362 and/or between fluorophore 342 and photodetector 364 and/or between fluorophore 362 and photodetector 344. Antenna may include any suitable material, such as, for example, titanium. or a titanium foil.

Electrode layer 307 may be disposed on antenna 306. Electrode layer 307 may define a conductive surface of medical device 300 that is configured to detect electrical signals within a human patient, such as, for example, ECG signals. Electrode layer 307 may include any suitable material, such as, for example, titanium nitride.

Figure 4:
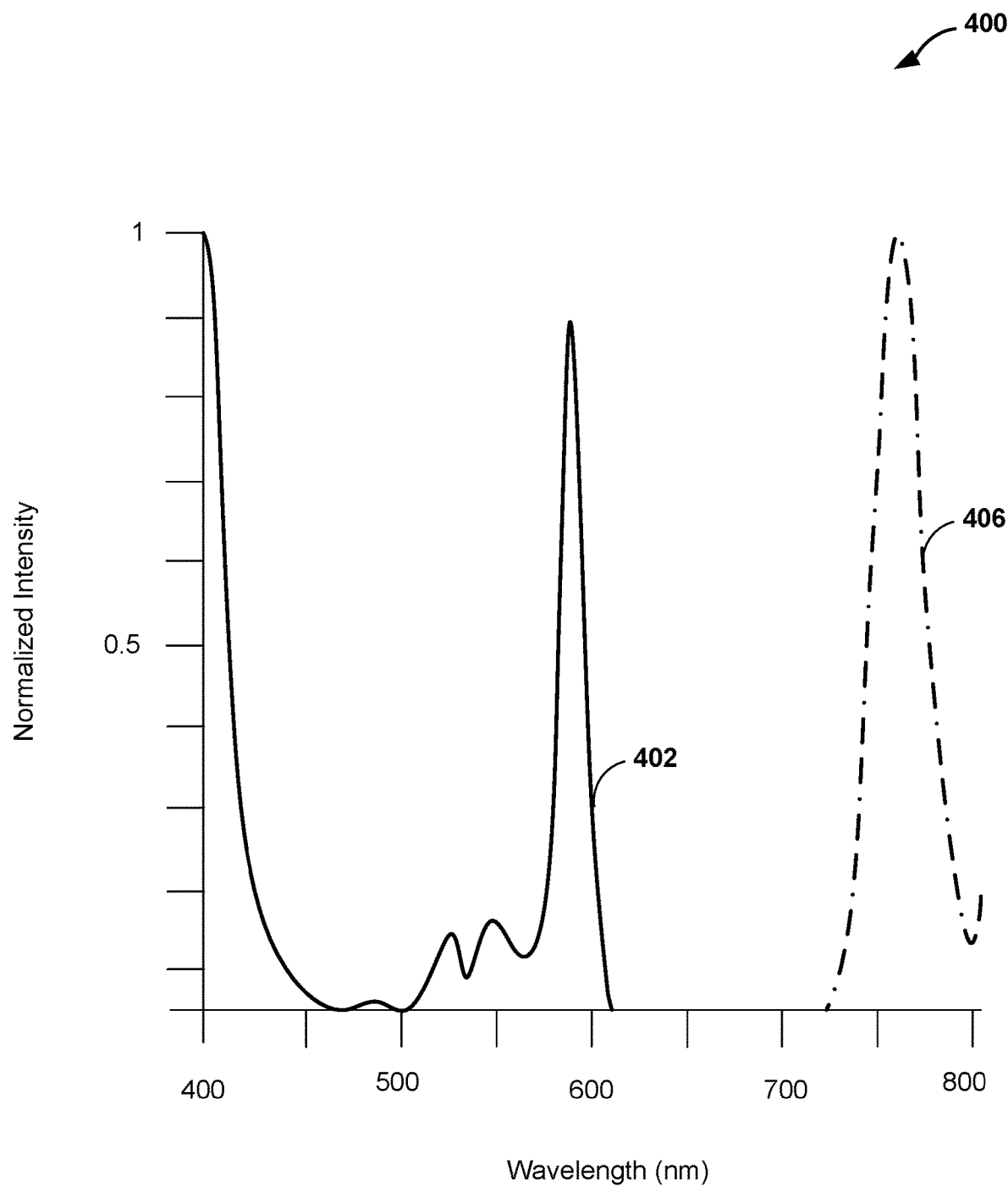
FIG. 4 is a graph illustrating an example absorption and emission spectrum of an optical sensor.

FIG. 4 is a graph 400 illustrating an example absorption and emission spectra of an optical sensor. The example absorption and emission spectrum may indicative of the absorption and emission of one or more of the fluorophores described above in reference to FIGS. 1 through 3. As illustrated in FIG. 4, the absorption and emission spectrums are plotted as wavelength versus normalized intensity. The wavelength is limited to a range between 400 nanometers (nm) and 800 nm. In some examples, at least a portion of the absorption and/or emission spectra may lie outside of the illustrated range.

Solid line 402 illustrates the example absorption of a fluorophore, which may include a peak absorption at or near 590 nm. Given a peak absorption at or near 590 nm, a light source may be selected to emit radiation at or near 590 nm.

In this way, matching or at least coordinating the fluorophore absorption spectrum and light source emission spectrum may reduce a duration of emission by the light source to achieve a selected absorption (and/or associated fluorescence emission) and/or an energy consumption by the light source to achieve the selected absorption (and/or associated fluorescence emission).

Dashed line 404 illustrates an example fluorescence emission by the fluorophore, which may include a peak emissivity at or near 760 nm. Given a peak emissivity at or near 760 nm, the photodetector of an optical beacon may be selected to detect radiation at or near 760 nm with greater sensitivity relative to wavelengths that are significantly shorter or longer, e.g., less than 700 nm (such as less than 400 nm or less than 600 nm) or greater than 800 nm (such as greater than 900 nm or greater than 1000 nm). In this way, matching or at least coordinating the detection sensitivity of a photodetector to the peak emissivity of the fluorophore may improve detection accuracy, and thereby improve an accuracy of the determination of an analyte concentration.

Figure 5:
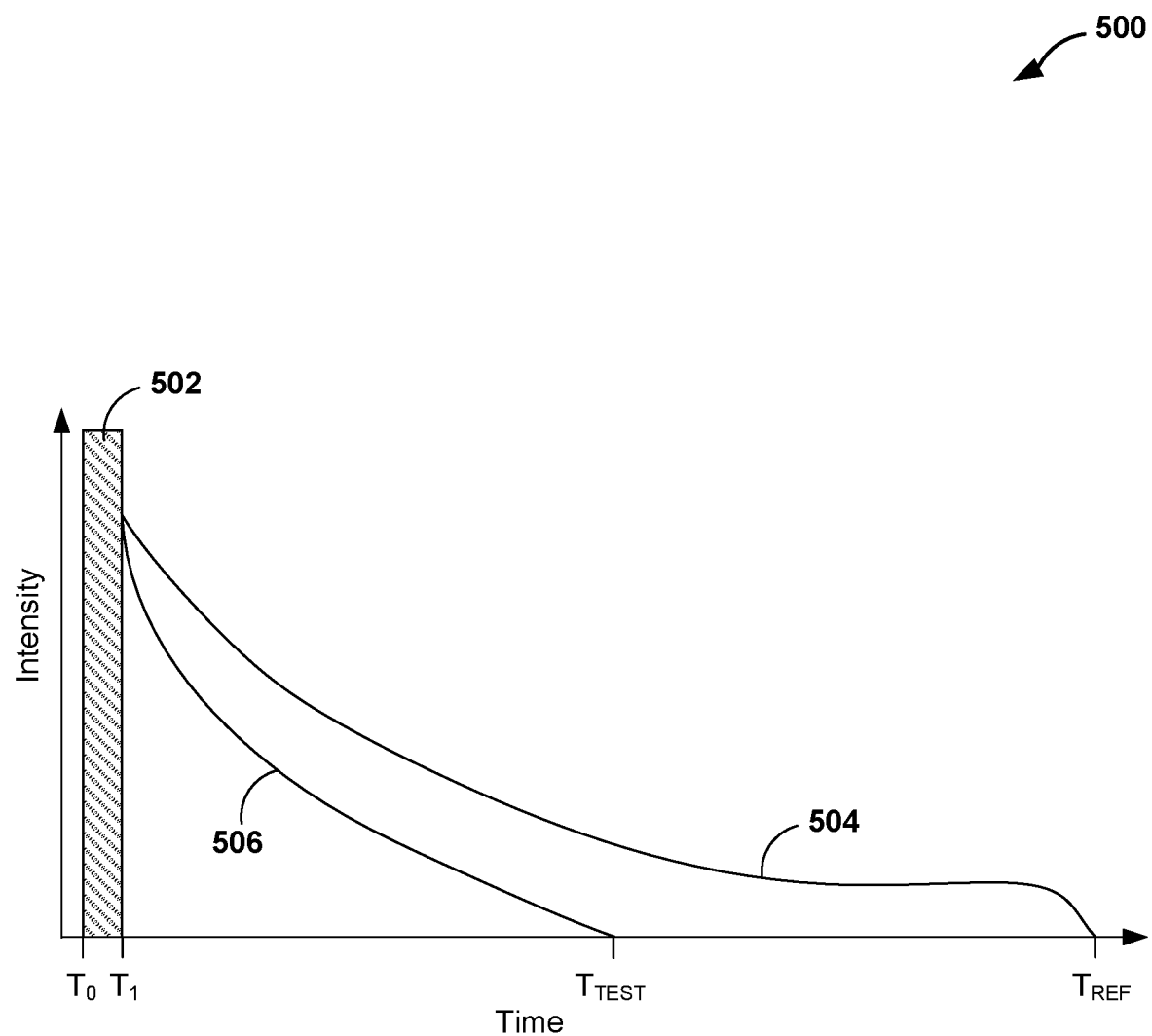
FIG. 5 is a graph illustrating time-domain filtering of an example fluorescence decay of an optical sensor.

FIG. 5 is a graph 500 illustrating time-domain filtering of an example fluorescence decay of an optical sensor, such as the example optical sensors describe above in reference to FIGS. 1-3. In some examples, a light source may be pulsed for a duration from $T_0$ to $T_1$, illustrated as pulse 502. The duration of pulse 502 may be within a range from about 1 millisecond (ms) to about 10 ms. In some examples, the duration of pulse 502 may be shorter than 1 ms or greater than 10 ms, such as greater than about 100 ms or greater than 1 second. In some examples, the pulse duration may be selected to result in a fluorescence of a fluorophore sufficient for detection by a photodetector. In some examples, the pulse duration may be selected to reduce power consumption by a light source.

The fluorescence decay 504 of reference optical beacon may include a duration from about $T_1$ to $T_{REF}$. The fluorescence decay 506 of test optical beacon may include a duration from about $T_1$ to $T_{TEST}$. In some examples, the intensity of both fluorescence decay 504 and fluorescence decay 506 over the respective duration may be stored, for example, by respective capacitors as discussed above. In this way, the stored electrical energy may be indicative of an integral of the respective fluorescence decay for the respective duration. The difference between the integrals of fluorescence decay 504 and fluorescence decay 506 may be indicative of a difference in a substance proximate reference optical beacon and test optical beacon, respectively. The difference may be indicative of an absolute difference or, in other examples, a ratio of fluorescence decay 504 and fluorescence decay 506 or other mathematical association between fluorescence decay 504 and fluorescence decay 506 that is indicative of the concentration of the analyte proximate each respective optical beacon. Hence, when the concentration of the substance proximal the respective optical beacon is associated (e.g., proportional) to the concentration of an analyte, the difference between the electrical energy stored in respective capacitors may be used to determine the concentration of the analyte.

Although described as including a single pulse 502, in other examples, two pulses may be used. For example, a first pulse may be used to generate fluorescence decay 504, and a second light pulse may be used to generate fluorescence decay 506. Additionally, or alternatively, the stored electrical energy may be sampled at discrete time intervals during an integration period to determine a light emission decay time constant. For example, the light emission decay time constant may be based on a rate of change of the stored electrical energy. The light emission decay time constant may be indicative of photo-bleaching of a fluorophore. In some examples, the light emission decay time constant may be used to mitigate the effect of photo-bleaching over time that would attenuate the overall signal amplitude.

Figure 6:
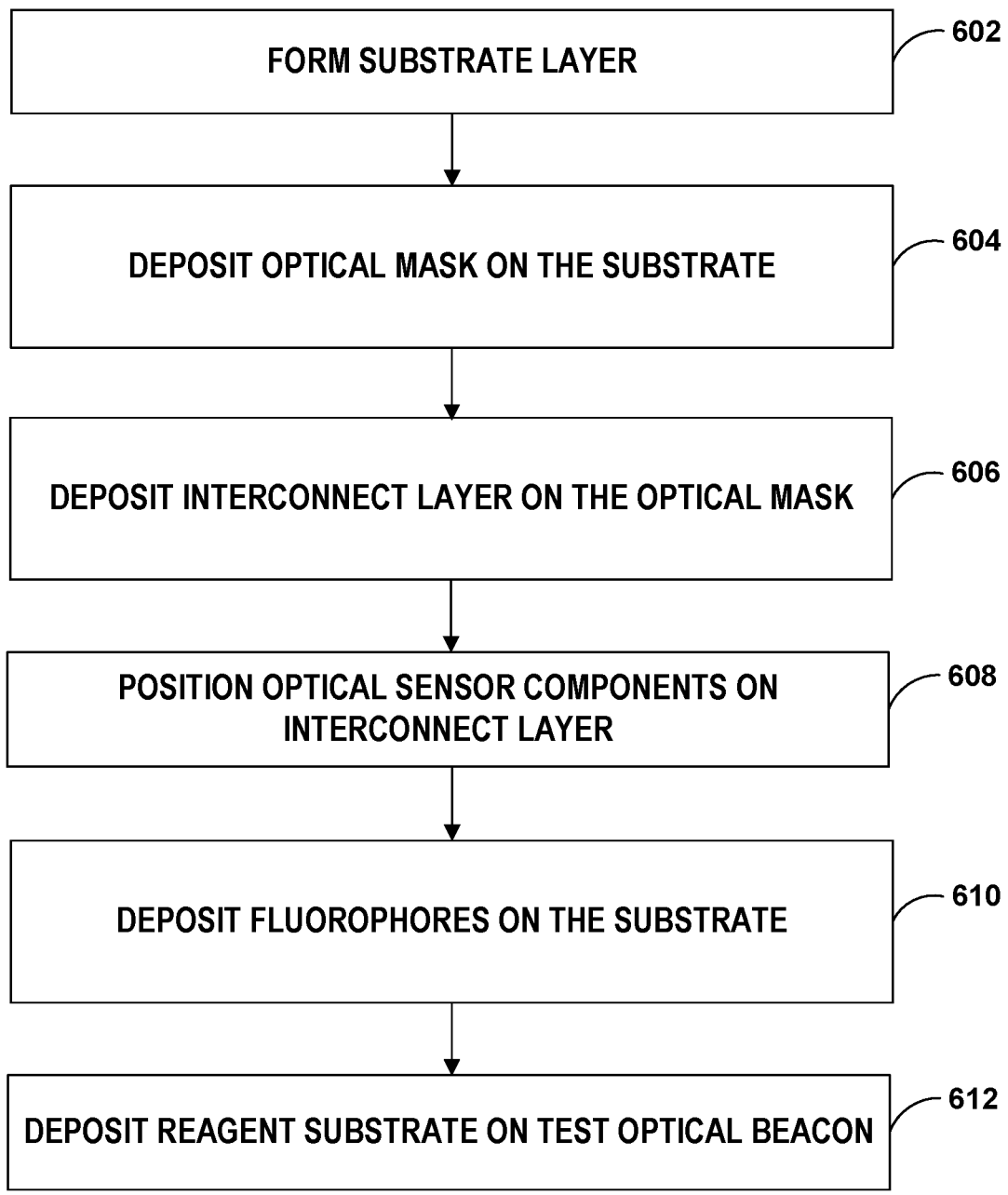
FIG. 6 is a flow diagram illustrating an example technique of forming an optical sensor.

The above described medical devices and optical sensors may be formed using any suitable technique. FIG. 6 is a flow diagram illustrating an example technique of forming an optical sensor. Although the technique illustrated in FIG. 6 will be described with respect to medical device 300 as illustrated in FIG. 3, in some examples, the technique may be used to form other medical devices, including, but not limited to, medical devices 100 and 200 illustrated in FIGS. 1 and 2.

The technique illustrated in FIG. 6 includes forming substrate layer 320 defining surface 322 (602). In some examples, forming substrate layer 320 may include forming surface features in substrate layer 320, such as, for example, optical barriers 330, by, for example, machining, laser etching, or chemical etching. In some examples, forming substrate layer 320 may include forming a plurality of regions each associated with substrate layer of a respective medical device.

The technique illustrated in FIG. 6 also includes depositing optical mask 318 on at least a portion of surface 322 to define surface 326 opposite surface 322 (604). Depositing optical mask 318 may include metallizing surface 322 by, for example, sputtering, chemical vapor deposition, physical vapor deposition, sputtering, thermal spraying, cold spraying, or the like. In some examples, depositing optical masking 318 may include sputtering columnar titanium oxide directly onto surface 322 (e.g., nominal thickness within a range from about 250 nm to about 500 nm), and optionally dry etching optical mask 318 to pattern surface 326. In some examples, depositing optical mask 318 may include polishing at least a portion of surface 326 or etching at least a portion of optical mask 318.

In some examples, the technique of FIG. 6 may include depositing interconnect layer 324 on surface 326 (606). In some examples, depositing interconnect layer 324 may include metallizing surface 326 by, for example, chemical vapor deposition, physical vapor deposition, sputtering, thermal spraying, cold spraying, or the like. In some examples, depositing interconnect layer 324 may include polishing or etching at least a portion of interconnect layer 324.

The technique illustrated in FIG. 6 also includes positioning light sources 312, reference electrode 314, and test optical beacon 316 on interconnect layer 324 (608). For example, as discussed above forming optical mask 318 and/or interconnect layer 324 may include forming apertures, which may be sized to receive one or more components of optical sensor 102.

Optionally, the technique may include forming antenna 306 and/or electrode layer 307 on substrate layer 320. In some examples, forming antenna 306 and/or electrode layer 307 may include metallizing surface 321 by, for example, chemical vapor deposition, physical vapor deposition, sputtering, thermal spraying, cold spraying, or the like. Additionally, the technique may optionally include etching at least a portion of antenna 306 and/or electrode layer 307.

After positioning light sources 312 and photodetectors 344 and 364, the technique may include forming fluorophores 342 and 362 on surface 321 of substrate layer 320 (610). Forming fluorophores 342 and 362 may include, for example, spray coating, spin coating, slot coating, or dip coating.

After forming fluorophore 362, the technique may include forming reagent substrate 360 on fluorophore 362 (610). Forming reagent substrate 360 may include, for example, spray coating, spin coating, slot coating, or dip coating. In examples in which fluorophore 362 and reagent substrate 360 include a single layer, the technique may include forming fluorophore 362 with reagent substrate 360.

In some examples, forming an optical sensor, as illustrated in FIG. 6, may be performed as part of a technique of forming a medical device.

Figure 7:
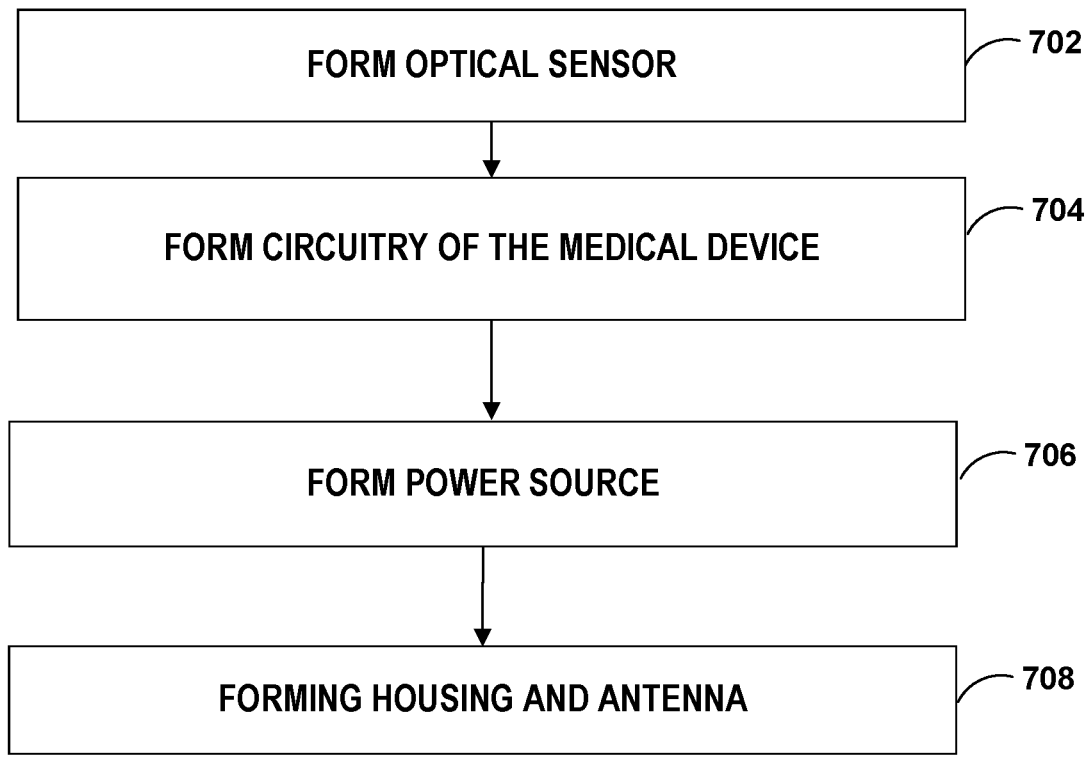
FIG. 7 is a flow diagram illustrating an example technique of forming a medical device including an optical sensor, processing circuitry, an antenna, and a power source.

FIG. 7 is a flow diagram illustrating an example technique of forming a medical device including an optical sensor, processing circuitry, an antenna, and a power source. Although the technique illustrated in FIG. 7 will be described with respect to medical device 100 illustrated FIG. 1, in some examples, the technique illustrated in FIG. 7 may be used to form other medical devices, including, but not limited to, medical devices 200 and 300 illustrated in FIGS. 2 and 3.

The technique illustrated in FIG. 7 includes forming optical sensor 302 (702). Prior to forming optical sensor 302, subsequent to forming optical sensor 302, or together with forming optical sensor 302, the technique includes forming circuitry on substrate layer 320 (704). In some examples, forming circuitry on substrate layer 320 may include forming a conductive circuit pattern on or in interconnect layer 324. In some examples, forming circuitry may include positioning a plurality of integrated chips on substrate layer 320 and/or interconnect layer 324. In some examples, each of the plurality of integrated chips may be positioned at correspond die locations on substrate layer 320. In some examples, a plurality of consecutive layers of a plurality of integrated chips may be positioned on substrate layer 320. For example, each consecutive layer of the plurality of consecutive layers may include one or more of processing circuitry 104, storage components 188, and communicant circuitry 190. Forming medical device 300 using consecutive layers may reduce a surface area of medical device 300 to facilitate implanting medical device 300 and/or improve patient comfort. In some examples, the circuitry may include individual circuit layouts (which are the same or substantially similar) for each respective die location (i.e., each respective medical device 300 of a plurality of medical devices). The circuitry for each die location includes electrically conductive traces, contact pads, and features designed for compatibility with the multilayer component stack to be mounted to the die location. Forming a plurality of medical devices may reduce manufacturing cost and/or time.

The technique of FIG. 7 also includes forming a power source (e.g., power source 108) (706). In some examples, forming power source 108 may include forming power source 108 on substrate layer 320. In some examples, forming power source 108 may include operatively coupling power source 108 to the circuitry, such as optical sensor 102, processing circuitry 104, storage components 188, or communicant circuitry 190. In some examples, forming power source 108 on substrate layer 320 may include positioning a plurality of power sources on substrate layer 320, the plurality of power sources corresponding to a respective die location or respective medical device.

The technique also includes forming housing 310 and antenna 306 (708). For example, substrate 320, optical sensor 302, power source 108, and associated circuitry may be disposed at least partially within housing 310. In some examples, antenna 306 may be formed on at least a portion of housing 310, and operatively coupled to the circuitry of medical device 300. In some examples, forming housing 310 may include forming a seal between one or more components of housing 310 and or components of medical device 300, such as components of optical sensor 302. The seal may be hermetic or non-hermetic. In examples in which the seal is hermetic, medical device 100 may have improved performance, improved device longevity, or both. In some examples, housing 310 may be attached to substrate layer 320 and/or other components of medical device 300 using an adhesive, epoxy, or other bond material. In this way, housing 310 may be configured to encapsulate components of medical device 300. In some examples, housing 310 may be configured to dissipate heat produced by components of medical device 300 (e.g., at power source 108). For example, housing 310 may include one or more baffles configured to improve heat transfer from power source 108 to an environment surrounding medical device 100 (e.g., sample fluid 101). By placing the cap wafer on power source 108, medical device 100 may reduce exposure of a patient to power source 108.

Figure 8:
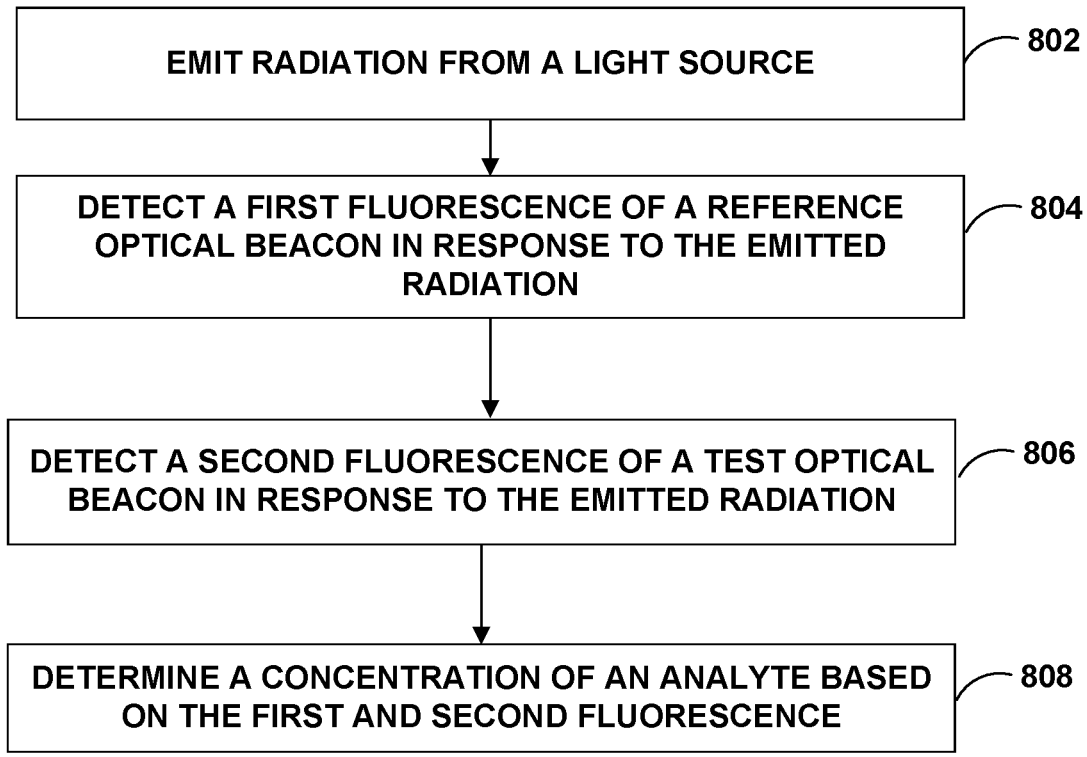
FIG. 8 is a flow diagram illustrating an example technique of detecting concentration of an analyte using an optical sensor.

FIG. 8 is a flow diagram illustrating an example technique of detecting a concentration of an analyte. Although the technique illustrated in FIG. 8 will be described with respect to medical device 100 illustrated in FIG. 1, in some examples, the technique illustrated in FIG. 8 may use other medical devices or other optical sensors to detect a concentration of an analyte, including, but not limited to, medical devices 200 and 300 illustrated in FIGS. 2 and 3.

The technique illustrated in FIG. 8 includes emitting, by a light source 112 of an optical sensor 102, a selected wavelength or wavelength range of radiation (802). As discussed above, light source 112 may include one or more LEDs, and emitting the radiation may include emitting from the one or more LEDs one or more wavelengths of radiation within a range from about 500 nm to about 680 nm. In some examples, the radiation may have a wavelength of about 590 nm, which can allow for less complex circuitry relative to, for example, LEDs configured to emit light having a wavelength greater than 590 nm. In some examples, processing circuitry 104 may be configured to control a timing of light pulse emitted by light source 112, such as a duration of pulse and/or a period of time between pulses.

The technique also includes detecting, by a photodetector (e.g., photodetector 344) of optical sensor 102, a first fluorescence emitted by a first fluorophore (e.g., fluorophore 342) of reference optical beacon 114 of optical sensor 102 in response to absorption of the radiation emitted by light source 112 (804). As discussed above, the first fluorescence is based on a first concentration of a substance proximate reference optical beacon 114. In some examples, the detecting may include storing, on a first capacitor, an electrical charge generated by the photodetector in response to the first fluorescence.

The technique also includes detecting, by a photodetector (e.g., photodetector 364), a second fluorescence emitted by a second fluorophore (e.g., fluorophore 362) of test optical beacon 116 of optical sensor 102 in response to absorption of the radiation emitted by light source 112 (806). As discussed above, the second fluorescence is based on a second concentration of the substance proximate test optical beacon 116. In some examples, the detecting may include storing, on a second capacitor, a second electrical charge generated by the photodetector in response to the second fluorescence. Additionally, test optical beacon 116 includes a reagent substrate (e.g., reagent substrate 360) that is configured to react with an analyte proximate the reagent substrate to produce the substance. Hence, the concentration of the substance proximate the second fluorophore is related to (e.g., proportional to) the concentration of the analyte.

Although described as including two photodetectors and, optionally, two capacitors, in some examples, optical sensor 102 may include a single photodetector and/or a single capacitor.

The technique also includes determining, processing circuitry 104 operatively coupled to optical sensor 102, based on the first fluorescence and the second fluorescence, a concentration of the analyte (808). For example, determining the concentration of the analyte may include determining a difference between the first fluorescence and the second fluorescence.

In some examples, the technique may include receiving, by processing circuitry 104 from one or more photodetectors (e.g., photodetectors 344 and/or 364), one or more signals indicative of a first intensity of the first fluorescence over a first duration of time and a second intensity of the second fluorescence over a second duration of time. In some examples, the first and second durations of time may be the same and/or overlap. For example, a single light pulse may be configured to be absorbed by both the first and second fluorophores. Alternatively, the first and second durations of time may be separate. The technique also may include determining, by processing circuitry 104, a first integral of the first intensity over the first duration of time. The technique also may include determining, by processing circuitry 104, a second integral of the second intensity over the second duration of time. As discussed above, determining the integrals of the first and second intensity may include storing, on at least one capacitor, the total electrical energy generated by the photodetector in response to the respective fluorescence. The technique also may include determining, by processing circuitry 104, e.g., via signal analysis module 198, a difference between the first integral and the second integral. For example, determining the difference between the first integral and the second integral may include determining, by processing circuitry 104, e.g., via signal analysis module 198, a difference between a first amount of energy stored on the capacitor and a second amount of energy stored on the capacitor. In some examples, the difference may be compared to predetermined values to determine a concentration of the analyte. For example, determining the analyte concentration may include, after determining a difference between the first integral and the second integral, comparing, by processing circuitry 104, e.g., via signal analysis module 198, the difference to predetermined differences associated with respective analyte concentration values. In some examples, the predetermined differences and respective analyte concentration values may be stored in, e.g., via signal analysis module 198, one or more lookup tables. Additionally, or alternatively, determining the analyte concentration may include, after determining a difference between the first integral and the second integral, determining, by processing circuitry 104, e.g., via signal analysis module 198, the analyte concentration based on an algorithm.

In some examples, the technique may include alerting a user of the analyte concentration. For example, external device 24 may receive an indication of the analyte concentration from processing circuitry 104, e.g., signal analysis module 198. In examples in which external device 24 includes a user interface, the technique amy include causing the user interface to generate an alert representative of the concentration of the analyte. The alert may be any type of information understandable by a human or machine, such as a user or another entity.

In some examples, the technique illustrated in FIG. 8 may be performed while medical device 100 is disposed within a biological system, such as inserted within an interstitial fluid of a human patient. In some examples, the technique illustrated in FIG. 8 optionally includes transmitting, by antenna 106 operatively coupled to processing circuitry 104, the determined concentration of the respective analyte to external device 24. In some examples, external device 24 may be located outside of the biological system, such as outside of the interstitial fluid of a human patient.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable media may include non-transitory computer-readable storage media and transient communication media. Computer readable storage media, which is tangible and non-transitory, may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer-readable storage media. It should be understood that the term "computer-readable storage media" refers to physical storage media, and not signals, carrier waves, or other transient media.

The following examples include subject matter of the present disclosure.

Example 1: A medical device comprising an optical sensor comprising a light source configured to emit radiation; a reference optical beacon comprising a first fluorophore configured to absorb at least a portion of the radiation emitted by the light source and emit, based on a first concentration of a substance proximate the reference optical beacon, a first fluorescence; a test optical beacon comprises a reagent substrate configured to react with an analyte proximate the reagent substrate to modulate a concentration of the substance; and a second fluorophore configured to absorb at least a portion of the radiation emitted by the light source and emit, based on a second concentration of the substance proximate the second fluorophore, a second fluorescence; and a photodetector configured to detect the first fluorescence and the second fluorescence; and processing circuitry operatively coupled to the optical sensor, wherein the processing circuitry is configured to: receive, from the optical sensor, one or more signals indicative of the first fluorescence and the second fluorescence; and determine, based on the one or more signals, a difference between the first fluorescence and the second fluorescence, wherein the difference is indicative of a concentration of the analyte.

Example 2: The medical device of example 1, wherein the reagent substrate comprises at least one enzyme configured to react with the analyte to modulate a concentration of the substance.

Example 3: The medical device of any of examples 1 and 2, wherein the substance comprises oxygen, wherein the analyte comprises glucose, and wherein the reagent substrate comprises: glucose oxidase, wherein the glucose oxidase is configured to convert the glucose into hydrogen peroxide; and catalase, wherein the catalase is configured to convert the hydrogen peroxide into oxygen.

Example 4: The medical device of any of examples 1 through 3, wherein the difference between the first fluorescence and the second fluorescence comprises a difference between a first integral of a first intensity of the first fluorescence over a duration of time and a second integral of a second intensity of the second fluorescence over the duration of time.

Example 5: The medical device of any of examples 1 through 4, wherein optical sensor further comprises an opaque material disposed between the reference optical beacon and the test optical beacon.

Example 6: The medical device of example 5, wherein the opaque material comprises titanium nitride.

Example 7: The medical device of any of examples 1 through 6, wherein the optical sensor further comprises a membrane configured to control diffusion of the analyte to the reagent substrate.

Example 8: The medical device of example 7, wherein the membrane comprises a light absorptive material.

Example 9: The medical device of any of examples 1 through 8, wherein the light source comprises one or more light emitting diodes configured to emit one or more wavelengths of radiation within a range from about 500 nm to about 680 nm.

Example 10: The medical device of any of examples 1 through 9, wherein the first fluorophore and the second fluorophore comprise the same material.

Example 11: The medical device of any of examples 1 through 10, wherein the first fluorophore and the second fluorophore comprises at least one of ruthenium-tris(4,7-diphenyl-1,10-phenanthroline) dichloride (Ru(dpp)), platinum(II) octaethylporphyrin (PtOEP), palladium(II) octaethylporphyrin (PdOEP), platinum(II)-5,10,15,20-tetrakis-(2,3,4,5,6-pentafluorphenyl)-porphyrin (PtTFPP), palladium(II)-5,10,15,20-tetrakis-(2,3,4,5,6-pentafluorphenyl)-porphyrin (PdTFPP), platinum(II) octaethylporphyrinketone (PtOEPK), palladium(II) octaethylporphyrinketone (PdOEPK), platinum(II) tetraphenyltetrabenzoporphyrin (PtTPTBP), palladium(II) tetraphenyltetrabenzoporphyrin (PtTPTBP), platinum(II) tetraphenyltetranaphthoporphyrin (PtPTPNP), or palladium(II) tetraphenyltetranaphthoporphyrin (PdPTPNP).

Example 12: The medical device of any of examples 1 through 11, further comprising an antenna operatively coupled to the processing circuitry, wherein the antenna is configured to transmit data representative of the concentration of the analyte to an external device.

Example 13: An optical sensor comprising: a light source configured to emit radiation; a reference optical beacon comprising a first fluorophore configured to absorb at least a portion of the radiation emitted by the light source and emit, based on a first concentration of a substance proximate the reference optical beacon, a first fluorescence; and a test optical beacon comprising a reagent substrate configured to react with an analyte proximate the reagent substrate to modulate a concentration of the substance; and a second fluorophore configured to absorb at least a portion of the radiation emitted by the light source and emit, based on a second concentration of the substance proximate the second fluorophore, a second fluorescence; and a photodetector configured to detect the first fluorescence and the second fluorescence, wherein the concentration of the analyte is related to a difference between the first fluorescence and the second fluorescence.

Example 14: The optical sensor of example 13, wherein the reagent substrate comprises at least one enzyme configured to react with the analyte to modulate a concentration of the substance.

Example 15: The optical sensor of any of examples 13 and 14, wherein the substance comprises oxygen, wherein the analyte comprises glucose, and wherein the reagent substrate comprises: glucose oxidase, wherein the glucose oxidase is configured to convert the glucose into hydrogen peroxide; and catalase, wherein the catalase is configured to convert the hydrogen peroxide into oxygen.

Example 16: The optical sensor of any of examples 13 through 15, further comprising an opaque material disposed between the reference optical beacon and the test optical beacon.

Example 17: The optical sensor of example 16, wherein the opaque material comprises titanium nitride.

Example 18: The optical sensor of any of examples 13 through 17, wherein the optical sensor further comprises a membrane configured to control diffusion of the analyte to the reagent substrate.

Example 19: The optical sensor of any of examples 13 through 18, wherein the membrane comprises a light absorptive material.

Example 20: The optical sensor of any of examples 13 through 19, wherein the light source comprises one or more light emitting diodes configured to emit one or more wavelengths of radiation within a range from about 500 nm to about 680 nm.

Example 21: The optical sensor of any of examples 13 through 20, wherein the first fluorophore and the second fluorophore comprise the same material.

Example 22: The optical sensor of any of examples 13 through 21, wherein the first fluorophore and the second fluorophore comprises at least one of ruthenium-tris(4,7-diphenyl-1,10-phenanthroline) dichloride (Ru(dpp)), platinum(II) octaethylporphyrin (PtOEP), palladium(II) octaethylporphyrin (PdOEP), platinum (II)-5,10,15,20-tetrakis-(2,3,4,5,6-pentafluorphenyl)-porphyrin (PtTFPP), palladium(II)-5,10,15,20-tetrakis-(2,3,4,5,6-pentafluorphenyl)-porphyrin (PdTFPP), platinum(II) octaethylporphyrinketone (PtOEPK), palladium(II) octaethylporphyrinketone (PdOEPK), platinum(II) tetraphenyltetrabenzoporphyrin (PtTPTBP), palladium(II) tetraphenyltetrabenzoporphyrin (PtTPTBP), platinum(II) tetraphenyltetranaphthoporphyrin (PtTPTNP), or palladium(II) tetraphenyltetranaphthoporphyrin (PdPTPNP).

Example 23: A method comprising: emitting, by a light source of an optical sensor, radiation; detecting, by a photodetector of the optical sensor, a first fluorescence emitted by a first fluorophore of a reference optical beacon of the optical sensor in response to absorption of the radiation emitted by the light source, wherein the first fluorescence is based on a first concentration of a substance proximate the reference optical beacon; detecting, by the photodetector, a second fluorescence emitted by a second fluorophore of a test optical beacon of the optical sensor in response to absorption of the radiation emitted by the light source, wherein the second fluorescence is based on a second concentration of the substance proximate the test optical beacon, wherein the test optical beacon comprises a reagent substrate configured to react with an analyte proximate the reagent substrate to modulate a concentration of the substance; and determining, by processing circuitry operatively coupled to the optical sensor, based on the first fluorescence and the second fluorescence, a concentration of the analyte.

Example 24: The method of example 23, wherein the light source comprises one or more light emitting diodes, wherein emitting the radiation comprises emitting from the one or more light emitting diodes one or more wavelengths of radiation within a range from about 500 nm to about 680 nm.

Example 25: The method of any of examples 23 and 24, wherein determining the concentration of the analyte comprises determining a difference between the first fluorescence and the second fluorescence.

Example 26: The method of any of examples 23 through 25, wherein determining the concentration of the analyte comprises: receiving, by the processing circuitry from the photodetector, one or more signals indicative of a first intensity of the first fluorescence over a duration of time and a second intensity of the second fluorescence over the duration of time; determining, by the processing circuitry, a first integral of the first intensity over the duration of time; determining by the processing circuitry, a second integral of the second intensity over the duration of time; and determining by the processing circuitry, a difference between the first integral and the second integral.

Example 27: The method of any of examples 23 through 26, wherein the method further comprises transmitting, by an antenna operatively coupled to the processing circuitry, the determined concentration of the analyte to an external device.

Example 28: The method of any of examples 23 through 27, further includes emitting, by the light source, a first pulse of light, wherein the first fluorescence is emitted in response to the first pulse of light; and emitting, by the light source, a second pulse of light a selected duration of time after the first pulse of light, wherein the second fluorescence is emitted in response to the second pulse of light.

Various examples have been described. These and other examples are within the scope of the following claims.

What is claimed is:
1. A medical device comprising:
an optical sensor comprising:
   a light source configured to emit radiation;
   a reference optical beacon comprising a first fluorophore configured to absorb at least a portion of the radiation emitted by the light source and emit, based on a first concentration of oxygen in a fluid proximate the reference optical beacon, a first fluorescence;
   a test optical beacon comprising:
     a reagent substrate configured to react with glucose proximate the reagent substrate to modulate a concentration of oxygen in the fluid, wherein the reagent substrate comprises:
       glucose oxidase, wherein the glucose oxidase is configured to oxidize the glucose to yield hydrogen peroxide; and
       catalase, wherein the catalase is configured to produce oxygen by reducing the hydrogen peroxide that the glucose oxidase yields into water and oxygen,
       wherein the reagent substrate is configured to modulate the concentration of oxygen in the fluid by consumption of oxygen by the glucose oxidase to oxidize the glucose and by production of oxygen by the catalase from the hydrogen peroxide that the glucose oxidase yields to generate a modulated concentration of oxygen in the fluid proximate a second fluorophore; and
     the second fluorophore configured to absorb at least a portion of the radiation emitted by the light source and emit, based on the modulated concentration of oxygen proximate the second fluorophore, a second fluorescence; and
   a photodetector configured to detect the first fluorescence and the second fluorescence; and
processing circuitry operatively coupled to the optical sensor, wherein the processing circuitry is configured to:
   receive, from the optical sensor, one or more signals indicative of the first fluorescence and the second fluorescence; and
   determine, based on the one or more signals, a difference between the first fluorescence and the second fluorescence, wherein the difference is indicative of a concentration of the glucose.

2. The medical device of claim 1, wherein the reagent substrate comprises at least one enzyme configured to react with the glucose to modulate a concentration of oxygen.

3. The medical device of claim 1, wherein the difference between the first fluorescence and the second fluorescence comprises a difference between a first integral of a first intensity of the first fluorescence over a duration of time and a second integral of a second intensity of the second fluorescence over the duration of time.

4. The medical device of claim 1, wherein optical sensor further comprises an opaque material disposed between the reference optical beacon and the test optical beacon.

5. The medical device of claim 4, wherein the opaque material comprises titanium nitride.

6. The medical device of claim 1, wherein the optical sensor further comprises a membrane configured to control diffusion of the glucose to the reagent substrate.

7. The medical device of claim 6, wherein the membrane comprises a light absorptive material.

8. The medical device of claim 1, wherein the light source comprises one or more light emitting diodes configured to emit one or more wavelengths of radiation within a range from 480 nm to 700 nm.

9. The medical device of claim 1, wherein a material of the first fluorophore and a material of the second fluorophore is the same.

10. The medical device of claim 1, wherein the first fluorophore and the second fluorophore comprises at least one of ruthenium-tris(4,7-diphenyl-1,10-phenanthroline) dichloride (Ru (dpp)), platinum (II) octaethylporphyrin (PtOEP), palladium (II) octaethylporphyrin (PdOEP), platinum (II)-5,10,15,20-tetrakis-(2,3,4,5,6-pentafluorphenyl)-porphyrin (PtTFPP), palladium (II)-5,10,15,20-tetrakis-(2,3,4,5,6-pentafluorphenyl)-porphyrin (PdTFPP), platinum (II) octaethylporphyrinketone (PtOEPK), palladium (II) octaethylporphyrinketone (PdOEPK), platinum (II) tetraphenyltetrabenzoporphyrin (PtTPTBP), palladium (II) tetraphenyltetrabenzoporphyrin (PtTPTBP), platinum (II) tetraphenyltetranaphthoporphyrin (PtPTPNP), or palladium (II) tetraphenyltetranaphthoporphyrin (PdPTPNP).

11. The medical device of claim 1, further comprising an antenna operatively coupled to the processing circuitry, wherein the antenna is configured to transmit data representative of the concentration of the glucose to an external device.

12. An optical sensor, comprising:
a light source configured to emit radiation;
a reference optical beacon comprising a first fluorophore configured to absorb at least a portion of the radiation emitted by the light source and emit, based on a first concentration of oxygen in a fluid proximate the reference optical beacon, a first fluorescence; and
a test optical beacon comprising:
a reagent substrate configured to react with glucose proximate the reagent substrate to modulate a concentration of oxygen in the fluid, wherein the reagent substrate comprises:
glucose oxidase, wherein the glucose oxidase is configured to oxidize the glucose to yield hydrogen peroxide; and
catalase, wherein the catalase is configured to produce oxygen by reducing the hydrogen peroxide that the glucose oxidase yields into water and oxygen,
wherein the reagent substrate is configured to modulate the concentration of oxygen in the fluid by consumption of oxygen by the glucose oxidase to oxidize the glucose and by production of oxygen by the catalase from the hydrogen peroxide that the glucose oxidase yields to generate a modulated concentration of oxygen in the fluid proximate a second fluorophore; and
the second fluorophore configured to absorb at least a portion of the radiation emitted by the light source and emit, based on the modulated concentration of oxygen proximate the second fluorophore, a second fluorescence; and
one or more photodetectors configured to detect the first fluorescence and the second fluorescence, wherein the concentration of the glucose is related to a difference between the first fluorescence and the second fluorescence.

13. The optical sensor of claim 12, wherein the reagent substrate comprises at least one enzyme configured to react with the glucose to modulate a concentration of oxygen.

14. The optical sensor of claim 12, further comprising an opaque material disposed between the reference optical beacon and the test optical beacon.

15. The optical sensor of claim 14, wherein the opaque material comprises titanium nitride.

16. The optical sensor of claim 12, wherein the optical sensor further comprises a membrane configured to control diffusion of the glucose to the reagent substrate.

17. The optical sensor of claim 12, wherein the membrane comprises a light absorptive material.

18. The optical sensor of claim 12, wherein the light source comprises one or more light emitting diodes configured to emit one or more wavelengths of radiation within a range from 480 nm to 700 nm.

19. The optical sensor of claim 12, wherein a material of the first fluorophore and a material of the second fluorophore is the same.

20. The optical sensor of claim 12, wherein the first fluorophore and the second fluorophore comprises at least one of ruthenium-tris(4,7-diphenyl-1,10-phenanthroline) dichloride (Ru(dpp)), platinum (II) octaethylporphyrin (PtOEP), palladium (II) octaethylporphyrin (PdOEP), platinum (II)-5,10,15,20-tetrakis-(2,3,4,5,6-pentafluorphenyl)-porphyrin (PtTFPP), palladium (II)-5,10,15,20-tetrakis-(2,3,4,5,6-pentafluorphenyl)-porphyrin (PdTFPP), platinum (II) octaethylporphyrinketone (PtOEPK), palladium (II) octaethylporphyrinketone (PdOEPK), platinum (II) tetraphenyltetrabenzoporphyrin (PtTPTBP), palladium (II) tetraphenyltetrabenzoporphyrin (PtTPTBP), platinum (II) tetraphenyltetranaphthoporphyrin (PtPTPNP), or palladium (II) tetraphenyltetranaphthoporphyrin (PdPTPNP).

21. A method, comprising:
emitting, by a light source of an optical sensor, radiation;
detecting, by a photodetector of the optical sensor, a first fluorescence emitted by a first fluorophore of a reference optical beacon of the optical sensor in response to absorption of the radiation emitted by the light source, wherein the first fluorescence is based on a first concentration of oxygen in a fluid proximate the reference optical beacon;
detecting, by the photodetector, a second fluorescence emitted by a second fluorophore of a test optical beacon of the optical sensor in response to absorption of the radiation emitted by the light source, wherein the second fluorescence is based on a modulated concentration of oxygen in the fluid proximate the test optical beacon, wherein the test optical beacon comprises a reagent substrate configured to react with glucose proximate the reagent substrate to modulate a concentration of oxygen in the fluid, wherein the reagent substrate comprises:
glucose oxidase, wherein the glucose oxidase is configured to oxidize the glucose to yield hydrogen peroxide; and
catalase, wherein the catalase is configured to produce oxygen by reducing the hydrogen peroxide that the glucose oxidase yields into water and oxygen,
wherein the reagent substrate is configured to modulate the concentration of oxygen in the fluid by consumption of oxygen by the glucose oxidase to oxidize the glucose and by production of oxygen by the catalase from the hydrogen peroxide that the glucose oxidase yields to generate the modulated concentration of oxygen in the fluid proximate the second fluorophore; and determining, by processing circuitry operatively coupled to the optical sensor, based on the first fluorescence and the second fluorescence, a concentration of the glucose.

22. The method of claim 21, wherein the light source comprises one or more light emitting diodes, wherein emitting the radiation comprises emitting from the one or more light emitting diodes one or more wavelengths of radiation within a range from 480 nm to 700 nm.

23. The method of claim 21, wherein determining the concentration of the glucose comprises determining a difference between the first fluorescence and the second fluorescence.

24. The method of claim 21, wherein determining the concentration of the glucose comprises:

receiving, by the processing circuitry from the photodetector, one or more signals indicative of a first intensity of the first fluorescence over a duration of time and a second intensity of the second fluorescence over the duration of time;

determining, by the processing circuitry, a first integral of the first intensity over the duration of time;

determining by the processing circuitry, a second integral of the second intensity over the duration of time; and determining by the processing circuitry, a difference between the first integral and the second integral.

25. The method of claim 21, wherein the method further comprises transmitting, by an antenna operatively coupled to the processing circuitry, the determined concentration of the glucose to an external device.

26. The method of claim 21, further comprising:

emitting, by the light source, a first pulse of light, wherein the first fluorescence is emitted in response to the first pulse of light; and emitting, by the light source, a second pulse of light a selected duration of time after the first pulse of light, wherein the second fluorescence is emitted in response to the second pulse of light.

* * * * *